US012781252B2

(12) United States Patent
Su et al.

(10) Patent No.: US 12,781,252 B2
(45) Date of Patent: Nov. 3, 2026

(54) STRAIN HAVING ENHANCED L-GLUTAMIC ACID PRODUCTIVITY, CONSTRUCTION METHOD THEREFOR AND APPLICATION THEREOF

(71) Applicant: NINGXIA EPPEN BIOTECH CO., LTD, Ningxia (CN)

(72) Inventors: Houbo Su, Ningxia (CN); Aiying Wei, Ningxia (CN); Gang Meng, Ningxia (CN); Lipeng Yang, Ningxia (CN); Fengyong Ma, Ningxia (CN); Huiping Jia, Ningxia (CN); Xiaoqun Zhou, Ningxia (CN); Chunguang Zhao, Ningxia (CN)

(73) Assignee: NINGXIA EPPEN BIOTECH CO., LTD, Ningxia (CN)

( * ) Notice: Subject to any disclaimer, the term of this patent is extended or adjusted under 35 U.S.C. 154(b) by 500 days.

(21) Appl. No.: 18/270,491

(22) PCT Filed: Dec. 29, 2021

(86) PCT No.: PCT/CN2021/142440
§ 371 (c)(1),
(2) Date: Jun. 30, 2023

(87) PCT Pub. No.: WO2022/143763
PCT Pub. Date: Jul. 7, 2022

(65) Prior Publication Data

US 2024/0067998 A1 Feb. 29, 2024

(30) Foreign Application Priority Data

Dec. 30, 2020 (CN) ......................... 202011631311.X

(51) Int. Cl.
*C12P 13/14* (2006.01)
*C07K 14/34* (2006.01)
*C12N 15/77* (2006.01)

(52) U.S. Cl.
CPC .............. *C12P 13/14* (2013.01); *C07K 14/34* (2013.01); *C12N 15/77* (2013.01)

(58) Field of Classification Search
None
See application file for complete search history.

(56) References Cited

FOREIGN PATENT DOCUMENTS

| | | | |
|---|---|---|---|
| CN | 1807634 | 7/2006 | |
| CN | 104093836 | 10/2014 | |
| CN | 109971660 | 7/2019 | |
| CN | 112646767 | 4/2021 | |
| KR | 20120046522 | 5/2012 | |
| KR | 20120140636 | 12/2012 | |
| WO | WO-0100844 A2 * | 1/2001 | .............. C12N 9/88 |
| WO | 2006028298 | 3/2006 | |
| WO | 2006100177 | 9/2006 | |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Accession A0A172QQ60. Sep. 7, 2016. (Year: 2016).*
Bornhorst et al. "Purification of proteins using polyhistidine affinity tags", Methods in Enzymology, Academic Press, vol. 326, 2000, pp. 245-254. (Year: 2000).*
"CdiA family toxin C-terminal domain-containing protein [Enterobacter roggenkampii]", NCBI Reference Sequence: WP_216312740.1, Jun. 18, 2021, pp. 1.
"NAD-dependent succinate-semialdehyde dehydrogenase [Corynebacterium glutamicum]", GenBank: QWQ83011.1, Jun. 15, 2021, pp. 1-2.
"NAD-dependent succinate-semialdehyde dehydrogenase[Corynebacterium glutamicum]", NCBI Reference Sequence: WP_011013348.1, Mar. 29, 2023, pp. 1-2.
Tuo Shi et al., "Mutation of genes for cell membrane synthesis in Corynebacterium glutamicum causes temperature-sensitive trait and promotes L-glutamate excretion", Biotechnology & Biotechnological Equipment, Jan. 16, 2020, pp. 38-47.
Chenglin Zhang et al., "Impact of 1dhA knockout on L-glutamate fermentation by Corynebacterium glutamicum TCCC 11822", China Brewing, Apr. 15, 2014, with English abstract, pp. 106-109, vol. 33, No. 4.
"International Search Report (Form PCT/ISA/210) of PCT/CN2021/142440", mailed on Apr. 1, 2022, with English translation thereof, pp. 1-8.
"Written Opinion of the International Searching Authority (Form PCT/ISA/237) of PCT/CN2021/142440", mailed on Apr. 1, 2022, pp. 1-5.

* cited by examiner

*Primary Examiner* — Christian L Fronda
(74) *Attorney, Agent, or Firm* — JCIPRNET

(57) ABSTRACT

Disclosed are strain having enhanced L-glutamic acid production capacity, and method for constructing the same and use thereof. A nucleotide sequence is provided by introducing a point mutation to a wild-type BBD29-00405 gene in *Corynebacterium glutamicum* so that the base at position 597 of SEQ ID NO: 1 is mutated from guanine (G) into adenine (A). Also provided is a recombinant strain obtained by introducing the polynucleotide sequence into L-glutamic acid-producing *Corynebacterium glutamicum*, the recombinant strain comprising a BBD29-00405 gene containing a point mutation. Compared with an unmodified strain, the resulting strain facilitates production of L-glutamic acid at a higher concentration.

1 Claim, No Drawings

Specification includes a Sequence Listing.

SEQUENCE LISTING

```
<160> NUMBER OF SEQ ID NOS: 49

<210> SEQ ID NO 1
<211> LENGTH: 1473
<212> TYPE: DNA
<213> ORGANISM: Corynebacterium glutamicum

<400> SEQUENCE: 1

atgactatta atgtctccga actacttgcc aaagtcccca cgggtctact gattggtgat      60

tcctgggtgg aagcatccga gggcggtact ttcgatgtgg aaaacccagc gacgggtgaa     120

acaatcgcaa cgctcgcgtc tgctacttcc gaggatgcac tggctgctct tgatgctgca     180
```

```
tgcgctgttc aggccgagtg ggctaggacg ccagcgcgcg agcgttctaa tattttacga    240

cgcggtttcg agctcgtcgc ggaacgtgca gaagagttcg ccaccctcat gaccttggaa    300

atgggcaaac ctttggctga agctcgcggc gaagtcacct acggcaacga attcctgcgc    360

tggttctctg aggaagcagt ccgcctctac ggccgctacg gtgctacccc agaaggcaac    420

ctgcgcatga tgaccacccg caaaccagtt ggcccctgcc tgttgatcac cccatggaac    480

ttcccactag caatggccac ccgtaaggtt gcacccgcca tcgctgcagg ttgtgtcatg    540

gtgctcaagc cagctcgcct gaccccgctg acctcccagt attttgccca gaccatgctt    600

gatgccggtc ttccagcagg tgtcctcaat gtggtctccg gtgcttccgc ctctgcgatt    660

tccaacccga ttatggaaga cgatcgcctt cgtaaagtct cattcaccgg ctccacccca    720

gttggccagc agctgctcaa aaaggctgcc gataaagttc tgcgcacctc catggaactc    780

ggcggcaacg cacctttcat tgtcttcgag gacgccgacc tagatctcgc gatcgaaggt    840

gccatgggcg caaaaatgcg caacatcggc gaagcttgca ccgcagccaa ccgtttccta    900

gtccacgaat ccgtcgccga tgaattcggc cgacgcttcg cagcccgcct cgaggaacaa    960

gtcctaggca acggcctcga cgaaggcgtc accgtaggcc cattggttga ggaaaaagca   1020

cgaaacagcg ttgcatcgct tgtcgacgcc gccgtctccg aaggtgccac cgtcctcacc   1080

ggtggcaagg ccggcacagg tgcaggctac ttctacgaac caacggtgct cacgggagtt   1140

tcaacagatg cagccatcct gaacgaagag atcttcggtc ccgtcgcacc gatcgtcacc   1200

ttctctgatg aagctgaagc tctgcgccta gccaattcca ccgaatacgg cctggcctcc   1260

tacgtgttca cccaagacac ctcacgcatc ttccgcgtct ccgacggcct cgagttcggc   1320

ctagtgggcg tcaactccgg tgtcatctct aacgccgctg caccttttgg tggcgtaaaa   1380

caatccggaa tgggccgcga aggtggtctc gaaggaattg aagagtacac ctccgtgcag   1440

tacatcggta tccgggatcc ttacgccggc tag                                1473
```

<210> SEQ ID NO 2
<211> LENGTH: 1473
<212> TYPE: DNA
<213> ORGANISM: Corynebacterium glutamicum

<400> SEQUENCE: 2

```
atgactatta atgtctccga actacttgcc aaagtcccca cgggtctact gattggtgat     60

tcctgggtgg aagcatccga gggcggtact ttcgatgtgg aaaacccagc gacgggtgaa    120

acaatcgcaa cgctcgcgtc tgctacttcc gaggatgcac tggctgctct tgatgctgca    180

tgcgctgttc aggccgagtg ggctaggacg ccagcgcgcg agcgttctaa tattttacga    240

cgcggtttcg agctcgtcgc ggaacgtgca gaagagttcg ccaccctcat gaccttggaa    300

atgggcaaac ctttggctga agctcgcggc gaagtcacct acggcaacga attcctgcgc    360

tggttctctg aggaagcagt ccgcctctac ggccgctacg gtgctacccc agaaggcaac    420

ctgcgcatga tgaccacccg caaaccagtt ggcccctgcc tgttgatcac cccatggaac    480

ttcccactag caatggccac ccgtaaggtt gcacccgcca tcgctgcagg ttgtgtcatg    540

gtgctcaagc cagctcgcct gaccccgctg acctcccagt attttgccca gaccatactt    600

gatgccggtc ttccagcagg tgtcctcaat gtggtctccg gtgcttccgc ctctgcgatt    660

tccaacccga ttatggaaga cgatcgcctt cgtaaagtct cattcaccgg ctccacccca    720

gttggccagc agctgctcaa aaaggctgcc gataaagttc tgcgcacctc catggaactc    780

ggcggcaacg cacctttcat tgtcttcgag gacgccgacc tagatctcgc gatcgaaggt    840
```

```
gccatgggcg caaaaatgcg caacatcggc gaagcttgca ccgcagccaa ccgtttccta    900

gtccacgaat ccgtcgccga tgaattcggc cgacgcttcg cagcccgcct cgaggaacaa    960

gtcctaggca acggcctcga cgaaggcgtc accgtaggcc cattggttga ggaaaaagca   1020

cgaaacagcg ttgcatcgct tgtcgacgcc gccgtctccg aaggtgccac cgtcctcacc   1080

ggtggcaagg ccggcacagg tgcaggctac ttctacgaac caacggtgct cacgggagtt   1140

tcaacagatg cagccatcct gaacgaagag atcttcggtc ccgtcgcacc gatcgtcacc   1200

ttctctgatg aagctgaagc tctgcgccta gccaattcca ccgaatacgg cctggcctcc   1260

tacgtgttca cccaagacac ctcacgcatc ttccgcgtct ccgacggcct cgagttcggc   1320

ctagtgggcg tcaactccgg tgtcatctct aacgccgctg caccttttgg tggcgtaaaa   1380

caatccggaa tgggccgcga aggtggtctc gaaggaattg aagagtacac ctccgtgcag   1440

tacatcggta tccgggatcc ttacgccggc tag                                 1473
```

```
<210> SEQ ID NO 3
<211> LENGTH: 490
<212> TYPE: PRT
<213> ORGANISM: Corynebacterium glutamicum

<400> SEQUENCE: 3

Met Thr Ile Asn Val Ser Glu Leu Leu Ala Lys Val Pro Thr Gly Leu
1               5                   10                  15

Leu Ile Gly Asp Ser Trp Val Glu Ala Ser Glu Gly Gly Thr Phe Asp
            20                  25                  30

Val Glu Asn Pro Ala Thr Gly Glu Thr Ile Ala Thr Leu Ala Ser Ala
        35                  40                  45

Thr Ser Glu Asp Ala Leu Ala Ala Leu Asp Ala Ala Cys Ala Val Gln
    50                  55                  60

Ala Glu Trp Ala Arg Thr Pro Ala Arg Glu Arg Ser Asn Ile Leu Arg
65                  70                  75                  80

Arg Gly Phe Glu Leu Val Ala Glu Arg Ala Glu Glu Phe Ala Thr Leu
                85                  90                  95

Met Thr Leu Glu Met Gly Lys Pro Leu Ala Glu Ala Arg Gly Glu Val
            100                 105                 110

Thr Tyr Gly Asn Glu Phe Leu Arg Trp Phe Ser Glu Glu Ala Val Arg
        115                 120                 125

Leu Tyr Gly Arg Tyr Gly Ala Thr Pro Glu Gly Asn Leu Arg Met Met
    130                 135                 140

Thr Thr Arg Lys Pro Val Gly Pro Cys Leu Leu Ile Thr Pro Trp Asn
145                 150                 155                 160

Phe Pro Leu Ala Met Ala Thr Arg Lys Val Ala Pro Ala Ile Ala Ala
                165                 170                 175

Gly Cys Val Met Val Leu Lys Pro Ala Arg Leu Thr Pro Leu Thr Ser
            180                 185                 190

Gln Tyr Phe Ala Gln Thr Met Leu Asp Ala Gly Leu Pro Ala Gly Val
        195                 200                 205

Leu Asn Val Val Ser Gly Ala Ser Ala Ser Ala Ile Ser Asn Pro Ile
    210                 215                 220

Met Glu Asp Asp Arg Leu Arg Lys Val Ser Phe Thr Gly Ser Thr Pro
225                 230                 235                 240

Val Gly Gln Gln Leu Leu Lys Lys Ala Ala Asp Lys Val Leu Arg Thr
                245                 250                 255
```

```
Ser Met Glu Leu Gly Gly Asn Ala Pro Phe Ile Val Phe Glu Asp Ala
            260                 265                 270

Asp Leu Asp Leu Ala Ile Glu Gly Ala Met Gly Ala Lys Met Arg Asn
        275                 280                 285

Ile Gly Glu Ala Cys Thr Ala Ala Asn Arg Phe Leu Val His Glu Ser
    290                 295                 300

Val Ala Asp Glu Phe Gly Arg Arg Phe Ala Ala Arg Leu Glu Glu Gln
305                 310                 315                 320

Val Leu Gly Asn Gly Leu Asp Glu Gly Val Thr Val Gly Pro Leu Val
                325                 330                 335

Glu Glu Lys Ala Arg Asn Ser Val Ala Ser Leu Val Asp Ala Ala Val
            340                 345                 350

Ser Glu Gly Ala Thr Val Leu Thr Gly Gly Lys Ala Gly Thr Gly Ala
        355                 360                 365

Gly Tyr Phe Tyr Glu Pro Thr Val Leu Thr Gly Val Ser Thr Asp Ala
    370                 375                 380

Ala Ile Leu Asn Glu Glu Ile Phe Gly Pro Val Ala Pro Ile Val Thr
385                 390                 395                 400

Phe Ser Asp Glu Ala Glu Ala Leu Arg Leu Ala Asn Ser Thr Glu Tyr
                405                 410                 415

Gly Leu Ala Ser Tyr Val Phe Thr Gln Asp Thr Ser Arg Ile Phe Arg
            420                 425                 430

Val Ser Asp Gly Leu Glu Phe Gly Leu Val Gly Val Asn Ser Gly Val
        435                 440                 445

Ile Ser Asn Ala Ala Ala Pro Phe Gly Gly Val Lys Gln Ser Gly Met
    450                 455                 460

Gly Arg Glu Gly Gly Leu Glu Gly Ile Glu Glu Tyr Thr Ser Val Gln
465                 470                 475                 480

Tyr Ile Gly Ile Arg Asp Pro Tyr Ala Gly
                485                 490


<210> SEQ ID NO 4
<211> LENGTH: 490
<212> TYPE: PRT
<213> ORGANISM: Corynebacterium glutamicum

<400> SEQUENCE: 4

Met Thr Ile Asn Val Ser Glu Leu Leu Ala Lys Val Pro Thr Gly Leu
1               5                   10                  15

Leu Ile Gly Asp Ser Trp Val Glu Ala Ser Glu Gly Gly Thr Phe Asp
            20                  25                  30

Val Glu Asn Pro Ala Thr Gly Glu Thr Ile Ala Thr Leu Ala Ser Ala
        35                  40                  45

Thr Ser Glu Asp Ala Leu Ala Ala Leu Asp Ala Ala Cys Ala Val Gln
    50                  55                  60

Ala Glu Trp Ala Arg Thr Pro Ala Arg Glu Arg Ser Asn Ile Leu Arg
65                  70                  75                  80

Arg Gly Phe Glu Leu Val Ala Glu Arg Ala Glu Glu Phe Ala Thr Leu
                85                  90                  95

Met Thr Leu Glu Met Gly Lys Pro Leu Ala Glu Ala Arg Gly Glu Val
            100                 105                 110

Thr Tyr Gly Asn Glu Phe Leu Arg Trp Phe Ser Glu Glu Ala Val Arg
        115                 120                 125

Leu Tyr Gly Arg Tyr Gly Ala Thr Pro Glu Gly Asn Leu Arg Met Met
    130                 135                 140
```

```
Thr Thr Arg Lys Pro Val Gly Pro Cys Leu Leu Ile Thr Pro Trp Asn
145                 150                 155                 160

Phe Pro Leu Ala Met Ala Thr Arg Lys Val Ala Pro Ala Ile Ala Ala
                165                 170                 175

Gly Cys Val Met Val Leu Lys Pro Ala Arg Leu Thr Pro Leu Thr Ser
            180                 185                 190

Gln Tyr Phe Ala Gln Thr Ile Leu Asp Ala Gly Leu Pro Ala Gly Val
        195                 200                 205

Leu Asn Val Val Ser Gly Ala Ser Ala Ser Ala Ile Ser Asn Pro Ile
    210                 215                 220

Met Glu Asp Asp Arg Leu Arg Lys Val Ser Phe Thr Gly Ser Thr Pro
225                 230                 235                 240

Val Gly Gln Gln Leu Leu Lys Lys Ala Ala Asp Lys Val Leu Arg Thr
                245                 250                 255

Ser Met Glu Leu Gly Gly Asn Ala Pro Phe Ile Val Phe Glu Asp Ala
            260                 265                 270

Asp Leu Asp Leu Ala Ile Glu Gly Ala Met Gly Ala Lys Met Arg Asn
        275                 280                 285

Ile Gly Glu Ala Cys Thr Ala Ala Asn Arg Phe Leu Val His Glu Ser
    290                 295                 300

Val Ala Asp Glu Phe Gly Arg Arg Phe Ala Ala Arg Leu Glu Glu Gln
305                 310                 315                 320

Val Leu Gly Asn Gly Leu Asp Glu Gly Val Thr Val Gly Pro Leu Val
                325                 330                 335

Glu Glu Lys Ala Arg Asn Ser Val Ala Ser Leu Val Asp Ala Ala Val
            340                 345                 350

Ser Glu Gly Ala Thr Val Leu Thr Gly Gly Lys Ala Gly Thr Gly Ala
        355                 360                 365

Gly Tyr Phe Tyr Glu Pro Thr Val Leu Thr Gly Val Ser Thr Asp Ala
    370                 375                 380

Ala Ile Leu Asn Glu Glu Ile Phe Gly Pro Val Ala Pro Ile Val Thr
385                 390                 395                 400

Phe Ser Asp Glu Ala Glu Ala Leu Arg Leu Ala Asn Ser Thr Glu Tyr
                405                 410                 415

Gly Leu Ala Ser Tyr Val Phe Thr Gln Asp Thr Ser Arg Ile Phe Arg
            420                 425                 430

Val Ser Asp Gly Leu Glu Phe Gly Leu Val Gly Val Asn Ser Gly Val
        435                 440                 445

Ile Ser Asn Ala Ala Ala Pro Phe Gly Gly Val Lys Gln Ser Gly Met
    450                 455                 460

Gly Arg Glu Gly Gly Leu Glu Gly Ile Glu Glu Tyr Thr Ser Val Gln
465                 470                 475                 480

Tyr Ile Gly Ile Arg Asp Pro Tyr Ala Gly
                485                 490


<210> SEQ ID NO 5
<211> LENGTH: 56
<212> TYPE: DNA
<213> ORGANISM: Artificial Sequence
<220> FEATURE:
<223> OTHER INFORMATION: Synthesized

<400> SEQUENCE: 5

cagtgccaag cttgcatgcc tgcaggtcga ctctagatga ctattaatgt ctccga        56
```

<210> SEQ ID NO 6
<211> LENGTH: 27
<212> TYPE: DNA
<213> ORGANISM: Artificial Sequence
<220> FEATURE:
<223> OTHER INFORMATION: Synthesized

<400> SEQUENCE: 6
agaccggcat caagtatggt ctgggca 27

<210> SEQ ID NO 7
<211> LENGTH: 27
<212> TYPE: DNA
<213> ORGANISM: Artificial Sequence
<220> FEATURE:
<223> OTHER INFORMATION: Synthesized

<400> SEQUENCE: 7
tgcccagacc atacttgatg ccggtct 27

<210> SEQ ID NO 8
<211> LENGTH: 62
<212> TYPE: DNA
<213> ORGANISM: Artificial Sequence
<220> FEATURE:
<223> OTHER INFORMATION: Synthesized

<400> SEQUENCE: 8
cagctatgac catgattacg aattcgagct cggtacccct agccggcgta aggatcccgg 60
at 62

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
agaaggcaac ctgcgcatga 20

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
atcgggttgg aaatcgcaga 20

<210> SEQ ID NO 11
<211> LENGTH: 56
<212> TYPE: DNA
<213> ORGANISM: Artificial Sequence
<220> FEATURE:
<223> OTHER INFORMATION: Synthesized

<400> SEQUENCE: 11
cagtgccaag cttgcatgcc tgcaggtcga ctctaggacc cgcttgccat acgaag 56

<210> SEQ ID NO 12
<211> LENGTH: 40
<212> TYPE: DNA
<213> ORGANISM: Artificial Sequence
<220> FEATURE:
<223> OTHER INFORMATION: Synthesized

<400> SEQUENCE: 12
cctaccacga cgagcactac atctactcat ctgaagaatc 40

<210> SEQ ID NO 13
<211> LENGTH: 40
<212> TYPE: DNA
<213> ORGANISM: Artificial Sequence
<220> FEATURE:
<223> OTHER INFORMATION: Synthesized

<400> SEQUENCE: 13
gattcttcag atgagtagat gtagtgctcg tcgtggtagg 40

<210> SEQ ID NO 14
<211> LENGTH: 40
<212> TYPE: DNA
<213> ORGANISM: Artificial Sequence
<220> FEATURE:
<223> OTHER INFORMATION: Synthesized

<400> SEQUENCE: 14
caaaccagag tgcccacgaa ctagccggcg taaggatccc 40

<210> SEQ ID NO 15
<211> LENGTH: 40
<212> TYPE: DNA
<213> ORGANISM: Artificial Sequence
<220> FEATURE:
<223> OTHER INFORMATION: Synthesized

<400> SEQUENCE: 15
gggatcctta cgccggctag ttcgtgggca ctctggtttg 40

<210> SEQ ID NO 16
<211> LENGTH: 58
<212> TYPE: DNA
<213> ORGANISM: Artificial Sequence
<220> FEATURE:
<223> OTHER INFORMATION: Synthesized

<400> SEQUENCE: 16
cagctatgac catgattacg aattcgagct cggtacccca taagaaacaa ccacttcc 58

<210> SEQ ID NO 17
<211> LENGTH: 20
<212> TYPE: DNA
<213> ORGANISM: Artificial Sequence
<220> FEATURE:
<223> OTHER INFORMATION: Synthesized

<400> SEQUENCE: 17
gtccaaggtg acggccgcac 20

<210> SEQ ID NO 18
<211> LENGTH: 20
<212> TYPE: DNA
<213> ORGANISM: Artificial Sequence
<220> FEATURE:
<223> OTHER INFORMATION: Synthesized

<400> SEQUENCE: 18
agcttcgccg atgttgcgca 20

<210> SEQ ID NO 19
<211> LENGTH: 23
<212> TYPE: DNA
<213> ORGANISM: Artificial Sequence
<220> FEATURE:
<223> OTHER INFORMATION: Synthesized

<400> SEQUENCE: 19
aggttgcacc cgccatcgct gca 23

<210> SEQ ID NO 20
<211> LENGTH: 20
<212> TYPE: DNA
<213> ORGANISM: Artificial Sequence
<220> FEATURE:
<223> OTHER INFORMATION: Synthesized

<400> SEQUENCE: 20
atattcggcc cagcagcagc 20

<210> SEQ ID NO 21
<211> LENGTH: 56
<212> TYPE: DNA
<213> ORGANISM: Artificial Sequence
<220> FEATURE:
<223> OTHER INFORMATION: Synthesized

<400> SEQUENCE: 21
gcttgcatgc ctgcaggtcg actctagagg atccccgtag tgctcgtcgt ggtagg 56

<210> SEQ ID NO 22
<211> LENGTH: 58
<212> TYPE: DNA
<213> ORGANISM: Artificial Sequence
<220> FEATURE:
<223> OTHER INFORMATION: Synthesized

<400> SEQUENCE: 22
atcaggctga aaatcttctc tcatccgcca aaacctagcc ggcgtaagga tcccggat 58

<210> SEQ ID NO 23
<211> LENGTH: 56
<212> TYPE: DNA
<213> ORGANISM: Artificial Sequence
<220> FEATURE:
<223> OTHER INFORMATION: Synthesized

<400> SEQUENCE: 23
cagtgccaag cttgcatgcc tgcaggtcga ctctaggtct gggggtgagc gcggat 56

<210> SEQ ID NO 24
<211> LENGTH: 54
<212> TYPE: DNA
<213> ORGANISM: Artificial Sequence
<220> FEATURE:
<223> OTHER INFORMATION: Synthesized

<400> SEQUENCE: 24
aggaaaataa cgcatccatc tgcccctta caaatccacc gcaaacactg ggat 54

<210> SEQ ID NO 25
<211> LENGTH: 54
<212> TYPE: DNA
<213> ORGANISM: Artificial Sequence
<220> FEATURE:
<223> OTHER INFORMATION: Synthesized

<400> SEQUENCE: 25
tggatttgta aaggggcaga tggatgcgtt attttccttc acttttcgta tcca 54

<210> SEQ ID NO 26
<211> LENGTH: 65
<212> TYPE: DNA
<213> ORGANISM: Artificial Sequence
<220> FEATURE:
<223> OTHER INFORMATION: Synthesized

<400> SEQUENCE: 26
cagctatgac catgattacg aattcgagct cggtacccct ctggcgcatc gaacaggtcg 60
aagga 65

<210> SEQ ID NO 27
<211> LENGTH: 20
<212> TYPE: DNA
<213> ORGANISM: Artificial Sequence
<220> FEATURE:
<223> OTHER INFORMATION: Synthesized

<400> SEQUENCE: 27
gtctgggggt gagcgcggat 20

<210> SEQ ID NO 28
<211> LENGTH: 27
<212> TYPE: DNA
<213> ORGANISM: Artificial Sequence
<220> FEATURE:
<223> OTHER INFORMATION: Synthesized

<400> SEQUENCE: 28
ctctggcgca tcgaacaggt cgaagga 27

<210> SEQ ID NO 29
<211> LENGTH: 647
<212> TYPE: DNA
<213> ORGANISM: Artificial Sequence
<220> FEATURE:
<223> OTHER INFORMATION: Synthesized

<400> SEQUENCE: 29
cagtgccaag cttgcatgcc tgcaggtcga ctctagatga ctattaatgt ctccgaacta 60
cttgccaaag tccccacggg tctactgatt ggtgattcct gggtggaagc atccgagggc 120
ggtactttcg atgtggaaaa cccagcgacg ggtgaaacaa tcgcaacgct cgcgtctgct 180
acttccgagg atgcactggc tgctcttgat gctgcatgcg ctgttcaggc cgagtgggct 240
aggacgccag cgcgcgagcg ttctaatatt ttacgacgcg gtttcgagct cgtcgcggaa 300
cgtgcagaag agttcgccac cctcatgacc ttggaaatgg gcaaaccttt ggctgaagct 360
cgcggcgaag tcacctacgg caacgaattc ctgcgctggt tctctgagga agcagtccgc 420
ctctacggcc gctacggtgc taccccagaa ggcaacctgc gcatgatgac cacccgcaaa 480
ccagttggcc cctgcctgtt gatcacccca tggaacttcc cactagcaat ggccacccgt 540
aaggttgcac ccgccatcgc tgcaggttgt gtcatggtgc tcaagccagc tcgcctgacc 600
ccgctgacct cccagtattt tgcccagacc atacttgatg ccggtct 647

<210> SEQ ID NO 30
<211> LENGTH: 927
<212> TYPE: DNA

<213> ORGANISM: Artificial Sequence
<220> FEATURE:
<223> OTHER INFORMATION: Synthesized

<400> SEQUENCE: 30
tgcccagacc atacttgatg ccggtcttcc agcaggtgtc ctcaatgtgg tctccggtgc 60
ttccgcctct gcgatttcca acccgattat ggaagacgat cgccttcgta aagtctcatt 120
caccggctcc accccagttg gccagcagct gctcaaaaag gctgccgata aagttctgcg 180
cacctccatg gaactcggcg gcaacgcacc tttcattgtc ttcgaggacg ccgacctaga 240
tctcgcgatc gaaggtgcca tgggcgcaaa aatgcgcaac atcggcgaag cttgcaccgc 300
agccaaccgt ttcctagtcc acgaatccgt cgccgatgaa ttcggccgac gcttcgcagc 360
ccgcctcgag gaacaagtcc taggcaacgg cctcgacgaa ggcgtcaccg taggcccatt 420
ggttgaggaa aaagcacgaa acagcgttgc atcgcttgtc gacgccgccg tctccgaagg 480
tgccaccgtc ctcaccggtg gcaaggccgg cacaggtgca ggctacttct acgaaccaac 540
ggtgctcacg ggagtttcaa cagatgcagc catcctgaac gaagagatct tcggtcccgt 600
cgcaccgatc gtcaccttct ctgatgaagc tgaagctctg cgcctagcca attccaccga 660
atacggcctg gcctcctacg tgttcaccca agacacctca cgcatcttcc gcgtctccga 720
cggcctcgag ttcggcctag tgggcgtcaa ctccggtgtc atctctaacg ccgctgcacc 780
ttttggtggc gtaaaacaat ccggaatggg ccgcgaaggt ggtctcgaag gaattgaaga 840
gtacacctcc gtgcagtaca tcggtatccg ggatccttac gccggctagg ggtaccgagc 900
tcgaattcgt aatcatggtc atagctg 927

<210> SEQ ID NO 31
<211> LENGTH: 1547
<212> TYPE: DNA
<213> ORGANISM: Artificial Sequence
<220> FEATURE:
<223> OTHER INFORMATION: Synthesized

<400> SEQUENCE: 31
cagtgccaag cttgcatgcc tgcaggtcga ctctagatga ctattaatgt ctccgaacta 60
cttgccaaag tccccacggg tctactgatt ggtgattcct gggtggaagc atccgagggc 120
ggtactttcg atgtggaaaa cccagcgacg ggtgaaacaa tcgcaacgct cgcgtctgct 180
acttccgagg atgcactggc tgctcttgat gctgcatgcg ctgttcaggc cgagtgggct 240
aggacgccag cgcgcgagcg ttctaatatt ttacgacgcg gtttcgagct cgtcgcggaa 300
cgtgcagaag agttcgccac cctcatgacc ttggaaatgg gcaaaccttt ggctgaagct 360
cgcggcgaag tcacctacgg caacgaattc ctgcgctggt tctctgagga agcagtccgc 420
ctctacggcc gctacggtgc taccccagaa ggcaacctgc gcatgatgac cacccgcaaa 480
ccagttggcc cctgcctgtt gatcacccca tggaacttcc cactagcaat ggccacccgt 540
aaggttgcac ccgccatcgc tgcaggttgt gtcatggtgc tcaagccagc tcgcctgacc 600
ccgctgacct cccagtattt tgcccagacc atacttgatg ccggtcttcc agcaggtgtc 660
ctcaatgtgg tctccggtgc ttccgcctct gcgatttcca acccgattat ggaagacgat 720
cgccttcgta aagtctcatt caccggctcc accccagttg gccagcagct gctcaaaaag 780
gctgccgata aagttctgcg cacctccatg gaactcggcg gcaacgcacc tttcattgtc 840
ttcgaggacg ccgacctaga tctcgcgatc gaaggtgcca tgggcgcaaa aatgcgcaac 900
atcggcgaag cttgcaccgc agccaaccgt ttcctagtcc acgaatccgt cgccgatgaa 960

```
ttcggccgac gcttcgcagc ccgcctcgag gaacaagtcc taggcaacgg cctcgacgaa   1020

ggcgtcaccg taggcccatt ggttgaggaa aaagcacgaa acagcgttgc atcgcttgtc   1080

gacgccgccg tctccgaagg tgccaccgtc ctcaccggtg gcaaggccgg cacaggtgca   1140

ggctacttct acgaaccaac ggtgctcacg ggagtttcaa cagatgcagc catcctgaac   1200

gaagagatct tcggtcccgt cgcaccgatc gtcaccttct ctgatgaagc tgaagctctg   1260

cgcctagcca attccaccga atacggcctg gcctcctacg tgttcaccca agacacctca   1320

cgcatcttcc gcgtctccga cggcctcgag ttcggcctag tgggcgtcaa ctccggtgtc   1380

atctctaacg ccgctgcacc ttttggtggc gtaaaacaat ccggaatggg ccgcgaaggt   1440

ggtctcgaag gaattgaaga gtacacctcc gtgcagtaca tcggtatccg ggatccttac   1500

gccggctagg ggtaccgagc tcgaattcgt aatcatggtc atagctg                 1547
```

```
<210> SEQ ID NO 32
<211> LENGTH: 1554
<212> TYPE: DNA
<213> ORGANISM: Artificial Sequence
<220> FEATURE:
<223> OTHER INFORMATION: Synthesized

<400> SEQUENCE: 32
```

```
cagtgccaag cttgcatgcc tgcaggtcga ctctagatga ctattaatgt ctccgaacta     60

cttgccaaag tccccacggg tctactgatt ggtgattcct gggtggaagc atccgagggc    120

ggtactttcg atgtggaaaa cccagcgacg ggtgaaacaa tcgcaacgct cgcgtctgct    180

acttccgagg atgcactggc tgctcttgat gctgcatgcg ctgttcaggc cgagtgggct    240

aggacgccag cgcgcgagcg ttctaatatt ttacgacgcg gtttcgagct cgtcgcggaa    300

cgtgcagaag agttcgccac cctcatgacc ttggaaatgg gcaaaccttt ggctgaagct    360

cgcggcgaag tcacctacgg caacgaattc ctgcgctggt tctctgagga agcagtccgc    420

ctctacggcc gctacggtgc taccccagaa ggcaacctgc gcatgatgac cacccgcaaa    480

ccagttggcc cctgcctgtt gatcacccca tggaacttcc cactagcaat ggccacccgt    540

aaggttgcac ccgccatcgc tgcaggttgt gtcatggtgc tcaagccagc tcgcctgacc    600

ccgctgacct cccagtattt tgcccagacc atacttgatg ccggtcttcc agcaggtgtc    660

ctcaatgtgg tctccggtgc ttccgcctct gcgatttcca acccgattat ggaagacgat    720

cgccttcgta aagtctcatt caccggctcc accccagttg gccagcagct gctcaaaaag    780

gctgccgata aagttctgcg cacctccatg gaactcggcg gcaacgcacc tttcattgtc    840

ttcgaggacg ccgacctaga tctcgcgatc gaaggtgcca tgggcgcaaa aatgcgcaac    900

atcggcgaag cttgcaccgc agccaaccgt ttcctagtcc acgaatccgt cgccgatgaa    960

ttcggccgac gcttcgcagc ccgcctcgag gaacaagtcc taggcaacgg cctcgacgaa   1020

ggcgtcaccg taggcccatt ggttgaggaa aaagcacgaa acagcgttgc atcgcttgtc   1080

gacgccgccg tctccgaagg tgccaccgtc ctcaccggtg gcaaggccgg cacaggtgca   1140

ggctacttct acgaaccaac ggtgctcacg ggagtttcaa cagatgcagc catcctgaac   1200

gaagagatct tcggtcccgt cgcaccgatc gtcaccttct ctgatgaagc tgaagctctg   1260

cgcctagcca attccaccga atacggcctg gcctcctacg tgttcaccca agacacctca   1320

cgcatcttcc gcgtctccga cggcctcgag ttcggcctag tgggcgtcaa ctccggtgtc   1380

atctctaacg ccgctgcacc ttttggtggc gtaaaacaat ccggaatggg ccgcgaaggt   1440
```

ggtctcgaag gaattgaaga gtacacctcc gtgcagtaca tcggtatccg ggatccttac 1500
gccggctagg ggtaccgagc tcgaattcgt aatcatggtc atagctgttt cctg 1554

<210> SEQ ID NO 33
<211> LENGTH: 261
<212> TYPE: DNA
<213> ORGANISM: Artificial Sequence
<220> FEATURE:
<223> OTHER INFORMATION: Synthesized

<400> SEQUENCE: 33
agaaggcaac ctgcgcatga tgaccacccg caaaccagtt ggcccctgcc tgttgatcac 60
cccatggaac ttcccactag caatggccac ccgtaaggtt gcacccgcca tcgctgcagg 120
ttgtgtcatg gtgctcaagc cagctcgcct gaccccgctg acctcccagt attttgccca 180
gaccatgctt gatgccggtc ttccagcagg tgtcctcaat gtggtctccg gtgcttccgc 240
ctctgcgatt tccaacccga t 261

<210> SEQ ID NO 34
<211> LENGTH: 806
<212> TYPE: DNA
<213> ORGANISM: Artificial Sequence
<220> FEATURE:
<223> OTHER INFORMATION: Synthesized

<400> SEQUENCE: 34
cagtgccaag cttgcatgcc tgcaggtcga ctctaggacc cgcttgccat acgaagtcct 60
ggagaagatc tccacccgca tcaccaacga agttccagac gtaaaccgcg tggttttgga 120
cgtaacctcc aagccaccag gaaccatcga atgggagtag gccttaaatg agccttcgtt 180
aagcggcaat caccttatcg gtgattgccg ctttcccatt tctccgggtt ttctggaact 240
ttttgggcgt atgctgggaa tgatcttatt attttgattt cagaaagcag gagagaccag 300
atgagcgaaa tccttgaaac ctactgggca ccccacttcg gaaacaccga tgaagccgca 360
gcactcgttt catacttggc acaagcttcc ggtgatccta ttgaggttca caccctgttc 420
ggggatttag gtttagacgg actctctgga aactacaccg acactgagat cgacggctac 480
ggcgacgcat tcctgctggt tgcagcacta gcagtgttga tggctgaaaa caaagcatcc 540
ggcggcgtga atctgggtga agttggggga gctgataaat cgatccggct gcatgttgaa 600
tccaaggaaa acacccagat caacaccgca ttgaagtact ttgcgctttc cccagaagac 660
cacgcagcgg cagatcgctt cgatgaggat gacctgtctg agcttgccaa cttgagtgaa 720
gagctgcgcg gacagctgga ctaattgctg cccgtttaag gagtccgatt cttcagatga 780
gtagatgtag tgctcgtcgt ggtagg 806

<210> SEQ ID NO 35
<211> LENGTH: 1777
<212> TYPE: DNA
<213> ORGANISM: Artificial Sequence
<220> FEATURE:
<223> OTHER INFORMATION: Synthesized

<400> SEQUENCE: 35
gattcttcag atgagtagat gtagtgctcg tcgtggtagg tgcgcagcag agattcaggc 60
gcacgaccag aaagcacgtg gctgagcttc cagccggacg ttgtggccgg agtaaaaatc 120
catccaaact ttccgcgatg ctggtaaacc tgtggatgtc aatgcctttg atttgaacta 180
agcacaggac tacctcgacg ccggcgccaa ctttgtccga gtcggtgccg atgtccagca 240
actcaacgct gctggatacg aaaagtgaag gaaaataacg catcatgact attaatgtct 300
ccgaactact tgccaaagtc cccacgggtc tactgattgg tgattcctgg gtggaagcat 360
ccgagggcgg tactttcgat gtggaaaacc cagcgacggg tgaaacaatc gcaacgctcg 420
cgtctgctac ttccgaggat gcactggctg ctcttgatgc tgcatgcgct gttcaggccg 480
agtgggctag gacgccagcg cgcgagcgtt ctaatatttt acgacgcggt ttcgagctcg 540
tcgcggaacg tgcagaagag ttcgccaccc tcatgacctt ggaaatgggc aaacctttgg 600
ctgaagctcg cggcgaagtc acctacggca acgaattcct gcgctggttc tctgaggaag 660
cagtccgcct ctacggccgc tacggtgcta ccccagaagg caacctgcgc atgatgacca 720
cccgcaaacc agttggcccc tgcctgttga tcaccccatg gaacttccca ctagcaatgg 780
ccacccgtaa ggttgcaccc gccatcgctg caggttgtgt catggtgctc aagccagctc 840
gcctgacccc gctgacctcc cagtattttg cccagaccat gcttgatgcc ggtcttccag 900
caggtgtcct caatgtggtc tccggtgctt ccgcctctgc gatttccaac ccgattatgg 960
aagacgatcg ccttcgtaaa gtctcattca ccggctccac cccagttggc cagcagctgc 1020
tcaaaaaggc tgccgataaa gttctgcgca cctccatgga actcggcggc aacgcacctt 1080
tcattgtctt cgaggacgcc gacctagatc tcgcgatcga aggtgccatg ggcgcaaaaa 1140
tgcgcaacat cggcgaagct tgcaccgcag ccaaccgttt cctagtccac gaatccgtcg 1200
ccgatgaatt cggccgacgc ttcgcagccc gcctcgagga acaagtccta ggcaacggcc 1260
tcgacgaagg cgtcaccgta ggcccattgg ttgaggaaaa agcacgaaac agcgttgcat 1320
cgcttgtcga cgccgccgtc tccgaaggtg ccaccgtcct caccggtggc aaggccggca 1380
caggtgcagg ctacttctac gaaccaacgg tgctcacggg agtttcaaca gatgcagcca 1440
tcctgaacga agagatcttc ggtcccgtcg caccgatcgt caccttctct gatgaagctg 1500
aagctctgcg cctagccaat tccaccgaat acggcctggc ctcctacgtg ttcacccaag 1560
acacctcacg catcttccgc gtctccgacg gcctcgagtt cggcctagtg ggcgtcaact 1620
ccggtgtcat ctctaacgcc gctgcacctt ttggtggcgt aaaacaatcc ggaatgggcc 1680
gcgaaggtgg tctcgaagga attgaagagt acacctccgt gcagtacatc ggtatccggg 1740
atccttacgc cggctagttc gtgggcactc tggtttg 1777

<210> SEQ ID NO 36
<211> LENGTH: 1777
<212> TYPE: DNA
<213> ORGANISM: Artificial Sequence
<220> FEATURE:
<223> OTHER INFORMATION: Synthesized

<400> SEQUENCE: 36
gattcttcag atgagtagat gtagtgctcg tcgtggtagg tgcgcagcag agattcaggc 60
gcacgaccag aaagcacgtg gctgagcttc cagccggacg ttgtggccgg agtaaaaatc 120
catccaaact ttccgcgatg ctggtaaacc tgtggatgtc aatgcctttg atttgaacta 180
agcacaggac tacctcgacg ccggcgccaa ctttgtccga gtcggtgccg atgtccagca 240
actcaacgct gctggatacg aaaagtgaag gaaaataacg catcatgact attaatgtct 300
ccgaactact tgccaaagtc cccacgggtc tactgattgg tgattcctgg gtggaagcat 360
ccgagggcgg tactttcgat gtggaaaacc cagcgacggg tgaaacaatc gcaacgctcg 420
cgtctgctac ttccgaggat gcactggctg ctcttgatgc tgcatgcgct gttcaggccg 480
agtgggctag gacgccagcg cgcgagcgtt ctaatatttt acgacgcggt ttcgagctcg 540
tcgcggaacg tgcagaagag ttcgccaccc tcatgacctt ggaaatgggc aaacctttgg 600
ctgaagctcg cggcgaagtc acctacggca acgaattcct gcgctggttc tctgaggaag 660
cagtccgcct ctacggccgc tacggtgcta ccccagaagg caacctgcgc atgatgacca 720
cccgcaaacc agttggcccc tgcctgttga tcaccccatg gaacttccca ctagcaatgg 780
ccacccgtaa ggttgcaccc gccatcgctg caggttgtgt catggtgctc aagccagctc 840
gcctgacccc gctgacctcc cagtattttg cccagaccat acttgatgcc ggtcttccag 900
caggtgtcct caatgtggtc tccggtgctt ccgcctctgc gatttccaac ccgattatgg 960
aagacgatcg ccttcgtaaa gtctcattca ccggctccac cccagttggc cagcagctgc 1020
tcaaaaaggc tgccgataaa gttctgcgca cctccatgga actcggcggc aacgcacctt 1080
tcattgtctt cgaggacgcc gacctagatc tcgcgatcga aggtgccatg ggcgcaaaaa 1140
tgcgcaacat cggcgaagct tgcaccgcag ccaaccgttt cctagtccac gaatccgtcg 1200
ccgatgaatt cggccgacgc ttcgcagccc gcctcgagga acaagtccta ggcaacggcc 1260
tcgacgaagg cgtcaccgta ggcccattgg ttgaggaaaa agcacgaaac agcgttgcat 1320
cgcttgtcga cgccgccgtc tccgaaggtg ccaccgtcct caccggtggc aaggccggca 1380
caggtgcagg ctacttctac gaaccaacgg tgctcacggg agtttcaaca gatgcagcca 1440
tcctgaacga agagatcttc ggtcccgtcg caccgatcgt caccttctct gatgaagctg 1500
aagctctgcg cctagccaat tccaccgaat acggcctggc ctcctacgtg ttcacccaag 1560
acacctcacg catcttccgc gtctccgacg gcctcgagtt cggcctagtg ggcgtcaact 1620
ccggtgtcat ctctaacgcc gctgcacctt ttggtggcgt aaaacaatcc ggaatgggcc 1680
gcgaaggtgg tctcgaagga attgaagagt acacctccgt gcagtacatc ggtatccggg 1740
atccttacgc cggctagttc gtgggcactc tggtttg 1777

<210> SEQ ID NO 37
<211> LENGTH: 788
<212> TYPE: DNA
<213> ORGANISM: Artificial Sequence
<220> FEATURE:
<223> OTHER INFORMATION: Synthesized

<400> SEQUENCE: 37
gggatcctta cgccggctag ttcgtgggca ctctggtttg gttaccagga tgggttagtc 60
attctgatca gcgaattcca cgttcacatc gccaattcca gagttcacaa ccagattcag 120
cattggacct tctagatcag cattgtgggc ggtgagatct ccaacatcac agcgcgctgt 180
gcccacaccg gcggtacaac ttaggctcac gggcacatca tcgggcaggg tgaccatgac 240
ttcgccgatc cctgaggtga tttggatgtt ttgttcctga tccaattggg tgaggtggct 300
gaaatcgagg ttcatttcac ccacgccaga ggtgtagctg ctgaggagtt catcgttggt 360
ggggatgaga ttgacatcgc cgattccagg gtcgtcttca aagtagatgg gatcgatatt 420
tgaaataaac aggcctgcga gggcgctcat gacaactccg gtaccaacta caccgccgac 480
aatccatggc cacacatggc gctttttctg aggcttttgt ggagggactt gtacatccca 540
ggtgttgtat tggttttggg caagtggatc ccaatgaggc gcttcggggg tttgttgcgc 600
gaagggtgca tagtagccct caacgggggt gatagtgctt agatctggtt ggggttgtgg 660
gtagagatct tcgtttttca tggtggcatc ctcagaaaca gtgaattcag tggtgagtag 720
tccgcggggt ggaagtggtt gtttcttatg ggtaccgag ctcgaattcg taatcatggt 780
catagctg 788

<210> SEQ ID NO 38
<211> LENGTH: 3291
<212> TYPE: DNA
<213> ORGANISM: Artificial Sequence
<220> FEATURE:
<223> OTHER INFORMATION: Synthesized

<400> SEQUENCE: 38
cagtgccaag cttgcatgcc tgcaggtcga ctctaggacc cgcttgccat acgaagtcct 60
ggagaagatc tccacccgca tcaccaacga agttccagac gtaaaccgcg tggttttgga 120
cgtaacctcc aagccaccag gaaccatcga atgggagtag gccttaaatg agccttcgtt 180
aagcggcaat caccttatcg gtgattgccg ctttcccatt tctccgggtt ttctggaact 240
ttttgggcgt atgctgggaa tgatcttatt attttgattt cagaaagcag gagagaccag 300
atgagcgaaa tccttgaaac ctactgggca ccccacttcg gaaacaccga tgaagccgca 360
gcactcgttt catacttggc acaagcttcc ggtgatccta ttgaggttca caccctgttc 420
ggggatttag gtttagacgg actctctgga aactacaccg acactgagat cgacggctac 480
ggcgacgcat tcctgctggt tgcagcacta gcagtgttga tggctgaaaa caaagcatcc 540
ggcggcgtga atctgggtga agttgggggga gctgataaat cgatccggct gcatgttgaa 600
tccaaggaaa acacccagat caacaccgca ttgaagtact ttgcgctttc cccagaagac 660
cacgcagcgg cagatcgctt cgatgaggat gacctgtctg agcttgccaa cttgagtgaa 720
gagctgcgcg gacagctgga ctaattgctg cccgtttaag gagtccgatt cttcagatga 780
gtagatgtag tgctcgtcgt ggtaggtgcg cagcagagat tcaggcgcac gaccagaaag 840
cacgtggctg agcttccagc cggacgttgt ggccggagta aaaatccatc caaactttcc 900
gcgatgctgg taaacctgtg gatgtcaatg cctttgattt gaactaagca caggactacc 960
tcgacgccgg cgccaacttt gtccgagtcg gtgccgatgt ccagcaactc aacgctgctg 1020
gatacgaaaa gtgaaggaaa ataacgcatc atgactatta atgtctccga actacttgcc 1080
aaagtcccca cgggtctact gattggtgat tcctgggtgg aagcatccga gggcggtact 1140
ttcgatgtgg aaaacccagc gacgggtgaa acaatcgcaa cgctcgcgtc tgctacttcc 1200
gaggatgcac tggctgctct tgatgctgca tgcgctgttc aggccgagtg ggctaggacg 1260
ccagcgcgcg agcgttctaa tattttacga cgcggtttcg agctcgtcgc ggaacgtgca 1320
gaagagttcg ccaccctcat gaccttggaa atgggcaaac ctttggctga agctcgcggc 1380
gaagtcacct acggcaacga attcctgcgc tggttctctg aggaagcagt ccgcctctac 1440
ggccgctacg gtgctacccc agaaggcaac ctgcgcatga tgaccacccg caaaccagtt 1500
ggcccctgcc tgttgatcac cccatggaac ttcccactag caatggccac ccgtaaggtt 1560
gcacccgcca tcgctgcagg ttgtgtcatg gtgctcaagc cagctcgcct gaccccgctg 1620
acctcccagt attttgccca gaccatgctt gatgccggtc ttccagcagg tgtcctcaat 1680
gtggtctccg gtgcttccgc ctctgcgatt tccaacccga ttatggaaga cgatcgcctt 1740
cgtaaagtct cattcaccgg ctccacccca gttggccagc agctgctcaa aaaggctgcc 1800
gataaagttc tgcgcacctc catggaactc ggcggcaacg cacctttcat tgtcttcgag 1860
gacgccgacc tagatctcgc gatcgaaggt gccatgggcg caaaaaatgcg caacatcggc 1920 gaagcttgca ccgcagccaa ccgtttccta gtccacgaat ccgtcgccga tgaattcggc 1980

```
cgacgcttcg cagcccgcct cgaggaacaa gtcctaggca acggcctcga cgaaggcgtc   2040
accgtaggcc cattggttga ggaaaaagca cgaaacagcg ttgcatcgct tgtcgacgcc   2100
gccgtctccg aaggtgccac cgtcctcacc ggtggcaagg ccggcacagg tgcaggctac   2160
ttctacgaac caacggtgct cacgggagtt tcaacagatg cagccatcct gaacgaagag   2220
atcttcggtc ccgtcgcacc gatcgtcacc ttctctgatg aagctgaagc tctgcgccta   2280
gccaattcca ccgaatacgg cctggcctcc tacgtgttca cccaagacac ctcacgcatc   2340
ttccgcgtct ccgacggcct cgagttcggc ctagtgggcg tcaactccgg tgtcatctct   2400
aacgccgctg caccttttgg tggcgtaaaa caatccggaa tgggccgcga aggtggtctc   2460
gaaggaattg aagagtacac ctccgtgcag tacatcggta tccgggatcc ttacgccggc   2520
tagttcgtgg gcactctggt ttggttacca ggatgggtta gtcattctga tcagcgaatt   2580
ccacgttcac atcgccaatt ccagagttca caaccagatt cagcattgga ccttctagat   2640
cagcattgtg ggcggtgaga tctccaacat cacagcgcgc tgtgcccaca ccggcggtac   2700
aacttaggct cacgggcaca tcatcgggca gggtgaccat gacttcgccg atccctgagg   2760
tgatttggat gttttgttcc tgatccaatt gggtgaggtg gctgaaatcg aggttcattt   2820
cacccacgcc agaggtgtag ctgctgagga gttcatcgtt ggtggggatg agattgacat   2880
cgccgattcc agggtcgtct tcaaagtaga tgggatcgat atttgaaata aacaggcctg   2940
cgagggcgct catgacaact ccggtaccaa ctacaccgcc gacaatccat ggccacacat   3000
ggcgcttttt ctgaggcttt tgtggaggga cttgtacatc ccaggtgttg tattggtttt   3060
gggcaagtgg atcccaatga ggcgcttcgg gggtttgttg cgcgaagggt gcatagtagc   3120
cctcaacggg ggtgatagtg cttagatctg gttggggttg tgggtagaga tcttcgtttt   3180
tcatggtggc atcctcagaa acagtgaatt cagtggtgag tagtccgcgg ggtggaagtg   3240
gttgtttctt atggggtacc gagctcgaat tcgtaatcat ggtcatagct g            3291
```

<210> SEQ ID NO 39
<211> LENGTH: 3291
<212> TYPE: DNA
<213> ORGANISM: Artificial Sequence
<220> FEATURE:
<223> OTHER INFORMATION: Synthesized

<400> SEQUENCE: 39

```
cagtgccaag cttgcatgcc tgcaggtcga ctctaggacc cgcttgccat acgaagtcct     60
ggagaagatc tccacccgca tcaccaacga agttccagac gtaaaccgcg tggttttgga    120
cgtaacctcc aagccaccag gaaccatcga atgggagtag gccttaaatg agccttcgtt    180
aagcggcaat caccttatcg gtgattgccg ctttcccatt tctccgggtt ttctggaact    240
ttttgggcgt atgctgggaa tgatcttatt attttgattt cagaaagcag gagagaccag    300
atgagcgaaa tccttgaaac ctactgggca ccccacttcg gaaacaccga tgaagccgca    360
gcactcgttt catacttggc acaagcttcc ggtgatccta ttgaggttca caccctgttc    420
ggggatttag gtttagacgg actctctgga aactacaccg acactgagat cgacggctac    480
ggcgacgcat tcctgctggt tgcagcacta gcagtgttga tggctgaaaa caaagcatcc    540
ggcggcgtga atctgggtga agttggggga gctgataaat cgatccggct gcatgttgaa    600
tccaaggaaa acacccagat caacaccgca ttgaagtact ttgcgctttc cccagaagac    660
cacgcagcgg cagatcgctt cgatgaggat gacctgtctg agcttgccaa cttgagtgaa    720
gagctgcgcg gacagctgga ctaattgctg cccgtttaag gagtccgatt cttcagatga    780
```

```
gtagatgtag tgctcgtcgt ggtaggtgcg cagcagagat tcaggcgcac gaccagaaag    840
cacgtggctg agcttccagc cggacgttgt ggccggagta aaaatccatc caaactttcc    900
gcgatgctgg taaacctgtg gatgtcaatg cctttgattt gaactaagca caggactacc    960
tcgacgccgg cgccaacttt gtccgagtcg gtgccgatgt ccagcaactc aacgctgctg   1020
gatacgaaaa gtgaaggaaa ataacgcatc atgactatta atgtctccga actacttgcc   1080
aaagtcccca cgggtctact gattggtgat tcctgggtgg aagcatccga gggcggtact   1140
ttcgatgtgg aaaacccagc gacgggtgaa acaatcgcaa cgctcgcgtc tgctacttcc   1200
gaggatgcac tggctgctct tgatgctgca tgcgctgttc aggccgagtg ggctaggacg   1260
ccagcgcgcg agcgttctaa tattttacga cgcggtttcg agctcgtcgc ggaacgtgca   1320
gaagagttcg ccaccctcat gaccttggaa atgggcaaac ctttggctga agctcgcggc   1380
gaagtcacct acggcaacga attcctgcgc tggttctctg aggaagcagt ccgcctctac   1440
ggccgctacg gtgctacccc agaaggcaac ctgcgcatga tgaccacccg caaaccagtt   1500
ggcccctgcc tgttgatcac cccatggaac ttcccactag caatggccac ccgtaaggtt   1560
gcacccgcca tcgctgcagg ttgtgtcatg gtgctcaagc cagctcgcct gaccccgctg   1620
acctcccagt attttgccca gaccatactt gatgccggtc ttccagcagg tgtcctcaat   1680
gtggtctccg gtgcttccgc ctctgcgatt tccaacccga ttatggaaga cgatcgcctt   1740
cgtaaagtct cattcaccgg ctccacccca gttggccagc agctgctcaa aaaggctgcc   1800
gataaagttc tgcgcacctc catggaactc ggcggcaacg cacctttcat tgtcttcgag   1860
gacgccgacc tagatctcgc gatcgaaggt gccatgggcg caaaaatgcg caacatcggc   1920
gaagcttgca ccgcagccaa ccgtttccta gtccacgaat ccgtcgccga tgaattcggc   1980
cgacgcttcg cagcccgcct cgaggaacaa gtcctaggca acggcctcga cgaaggcgtc   2040
accgtaggcc cattggttga ggaaaaagca cgaaacagcg ttgcatcgct tgtcgacgcc   2100
gccgtctccg aaggtgccac cgtcctcacc ggtggcaagg ccggcacagg tgcaggctac   2160
ttctacgaac caacggtgct cacgggagtt tcaacagatg cagccatcct gaacgaagag   2220
atcttcggtc ccgtcgcacc gatcgtcacc ttctctgatg aagctgaagc tctgcgccta   2280
gccaattcca ccgaatacgg cctggcctcc tacgtgttca cccaagacac ctcacgcatc   2340
ttccgcgtct ccgacggcct cgagttcggc ctagtgggcg tcaactccgg tgtcatctct   2400
aacgccgctg caccttttgg tggcgtaaaa caatccggaa tgggccgcga aggtggtctc   2460
gaaggaattg aagagtacac ctccgtgcag tacatcggta tccgggatcc ttacgccggc   2520
tagttcgtgg gcactctggt ttggttacca ggatgggtta gtcattctga tcagcgaatt   2580
ccacgttcac atcgccaatt ccagagttca caaccagatt cagcattgga ccttctagat   2640
cagcattgtg ggcggtgaga tctccaacat cacagcgcgc tgtgcccaca ccggcggtac   2700
aacttaggct cacgggcaca tcatcgggca gggtgaccat gacttcgccg atccctgagg   2760
tgatttggat gttttgttcc tgatccaatt gggtgaggtg gctgaaatcg aggttcattt   2820
cacccacgcc agaggtgtag ctgctgagga gttcatcgtt ggtggggatg agattgacat   2880
cgccgattcc agggtcgtct tcaaagtaga tgggatcgat atttgaaata aacaggcctg   2940
cgagggcgct catgacaact ccggtaccaa ctacaccgcc gacaatccat ggccacacat   3000
ggcgcttttt ctgaggcttt tgtggaggga cttgtacatc ccaggtgttg tattggtttt   3060
gggcaagtgg atcccaatga ggcgcttcgg gggtttgttg cgcgaagggt gcatagtagc   3120
```

```
cctcaacggg ggtgatagtg cttagatctg gttggggttg tgggtagaga tcttcgtttt   3180

tcatggtggc atcctcagaa acagtgaatt cagtggtgag tagtccgcgg ggtggaagtg   3240

gttgtttctt atggggtacc gagctcgaat tcgtaatcat ggtcatagct g            3291


<210> SEQ ID NO 40
<211> LENGTH: 1970
<212> TYPE: DNA
<213> ORGANISM: Artificial Sequence
<220> FEATURE:
<223> OTHER INFORMATION: Synthesized

<400> SEQUENCE: 40

gtccaaggtg acggccgcac ctacggacac ccaatcgtgc tgcgcccagt atcttccgaa     60

gacgcaatga ccgccgactg gacccgcttg ccatacgaag tcctggagaa gatctccacc    120

cgcatcacca acgaagttcc agacgtaaac cgcgtggttt tggacgtaac ctccaagcca    180

ccaggaacca tcgaatggga gtaggcctta aatgagcctt cgttaagcgg caatcacctt    240

atcggtgatt gccgctttcc catttctccg ggttttctgg aactttttgg gcgtatgctg    300

ggaatgatct tattattttg atttcagaaa gcaggagaga ccagatgagc gaaatccttg    360

aaacctactg ggcaccccac ttcggaaaca ccgatgaagc cgcagcactc gtttcatact    420

tggcacaagc ttccggtgat cctattgagg ttcacaccct gttcggggat ttaggtttag    480

acggactctc tggaaactac accgacactg agatcgacgg ctacggcgac gcattcctgc    540

tggttgcagc actagcagtg ttgatggctg aaaacaaagc atccggcggc gtgaatctgg    600

gtgaagttgg gggagctgat aaatcgatcc ggctgcatgt tgaatccaag gaaaacaccc    660

agatcaacac cgcattgaag tactttgcgc tttccccaga agaccacgca gcggcagatc    720

gcttcgatga ggatgacctg tctgagcttg ccaacttgag tgaagagctg cgcggacagc    780

tggactaatt gctgcccgtt taaggagtcc gattcttcag atgagtagat gtagtgctcg    840

tcgtggtagg tgcgcagcag agattcaggc gcacgaccag aaagcacgtg gctgagcttc    900

cagccggacg ttgtggccgg agtaaaaatc catccaaact ttccgcgatg ctggtaaacc    960

tgtggatgtc aatgcctttg atttgaacta agcacaggac tacctcgacg ccggcgccaa   1020

ctttgtccga gtcggtgccg atgtccagca actcaacgct gctggatacg aaaagtgaag   1080

gaaaataacg catcatgact attaatgtct ccgaactact tgccaaagtc cccacgggtc   1140

tactgattgg tgattcctgg gtggaagcat ccgagggcgg tactttcgat gtggaaaacc   1200

cagcgacggg tgaaacaatc gcaacgctcg cgtctgctac ttccgaggat gcactggctg   1260

ctcttgatgc tgcatgcgct gttcaggccg agtgggctag gacgccagcg cgcgagcgtt   1320

ctaatatttt acgacgcggt ttcgagctcg tcgcggaacg tgcagaagag ttcgccaccc   1380

tcatgacctt ggaaatgggc aaacctttgg ctgaagctcg cggcgaagtc acctacggca   1440

acgaattcct gcgctggttc tctgaggaag cagtccgcct ctacggccgc tacggtgcta   1500

ccccagaagg caacctgcgc atgatgacca cccgcaaacc agttggcccc tgcctgttga   1560

tcaccccatg gaacttccca ctagcaatgg ccacccgtaa ggttgcaccc gccatcgctg   1620

caggttgtgt catggtgctc aagccagctc gcctgacccc gctgacctcc cagtattttg   1680

cccagaccat gcttgatgcc ggtcttccag caggtgtcct caatgtggtc tccggtgctt   1740

ccgcctctgc gatttccaac ccgattatgg aagacgatcg ccttcgtaaa gtctcattca   1800

ccggctccac cccagttggc cagcagctgc tcaaaaaggc tgccgataaa gttctgcgca   1860

cctccatgga actcggcggc aacgcacctt tcattgtctt cgaggacgcc gacctagatc   1920
```

tcgcgatcga aggtgccatg ggcgcaaaaa tgcgcaacat cggcgaagct 1970

<210> SEQ ID NO 41
<211> LENGTH: 1758
<212> TYPE: DNA
<213> ORGANISM: Artificial Sequence
<220> FEATURE:
<223> OTHER INFORMATION: Synthesized

<400> SEQUENCE: 41
aggttgcacc cgccatcgct gcaggttgtg tcatggtgct caagccagct cgcctgaccc 60
cgctgacctc ccagtatttt gcccagacca tgcttgatgc cggtcttcca gcaggtgtcc 120
tcaatgtggt ctccggtgct tccgcctctg cgatttccaa cccgattatg gaagacgatc 180
gccttcgtaa agtctcattc accggctcca ccccagttgg ccagcagctg ctcaaaaagg 240
ctgccgataa agttctgcgc acctccatgg aactcggcgg caacgcacct ttcattgtct 300
tcgaggacgc cgacctagat ctcgcgatcg aaggtgccat gggcgcaaaa atgcgcaaca 360
tcggcgaagc ttgcaccgca gccaaccgtt tcctagtcca cgaatccgtc gccgatgaat 420
tcggccgacg cttcgcagcc cgcctcgagg aacaagtcct aggcaacggc ctcgacgaag 480
gcgtcaccgt aggcccattg gttgaggaaa aagcacgaaa cagcgttgca tcgcttgtcg 540
acgccgccgt ctccgaaggt gccaccgtcc tcaccggtgg caaggccggc acaggtgcag 600
gctacttcta cgaaccaacg gtgctcacgg gagtttcaac agatgcagcc atcctgaacg 660
aagagatctt cggtcccgtc gcaccgatcg tcaccttctc tgatgaagct gaagctctgc 720
gcctagccaa ttccaccgaa tacggcctgg cctcctacgt gttcacccaa gacacctcac 780
gcatcttccg cgtctccgac ggcctcgagt tcggcctagt gggcgtcaac tccggtgtca 840
tctctaacgc cgctgcacct tttggtggcg taaaacaatc cggaatgggc cgcgaaggtg 900
gtctcgaagg aattgaagag tacacctccg tgcagtacat cggtatccgg gatccttacg 960
ccggctagtt cgtgggcact ctggtttggt taccaggatg ggttagtcat tctgatcagc 1020
gaattccacg ttcacatcgc caattccaga gttcacaacc agattcagca ttggaccttc 1080
tagatcagca ttgtgggcgg tgagatctcc aacatcacag cgcgctgtgc ccacaccggc 1140
ggtacaactt aggctcacgg gcacatcatc gggcagggtg accatgactt cgccgatccc 1200
tgaggtgatt tggatgtttt gttcctgatc caattgggtg aggtggctga aatcgaggtt 1260
catttcaccc acgccagagg tgtagctgct gaggagttca tcgttggtgg ggatgagatt 1320
gacatcgccg attccagggt cgtcttcaaa gtagatggga tcgatatttg aaataaacag 1380
gcctgcgagg gcgctcatga caactccggt accaactaca ccgccgacaa tccatggcca 1440
cacatggcgc tttttctgag gcttttgtgg agggacttgt acatcccagg tgttgtattg 1500
gttttgggca agtggatccc aatgaggcgc ttcgggggtt tgttgcgcga agggtgcata 1560
gtagccctca acgggggtga tagtgcttag atctggttgg ggttgtgggt agagatcttc 1620
gtttttcatg gtggcatcct cagaaacagt gaattcagtg gtgagtagtc cgcggggtgg 1680
aagtggttgt ttcttatgca acgcccacca catggctaaa aggcaaaggt aagtaatggc 1740
tgctgctggg ccgaatat 1758

<210> SEQ ID NO 42
<211> LENGTH: 1807
<212> TYPE: DNA
<213> ORGANISM: Artificial Sequence
<220> FEATURE:

<223> OTHER INFORMATION: Synthesized

<400> SEQUENCE: 42
gcttgcatgc ctgcaggtcg actctagagg atccccgtag tgctcgtcgt ggtaggtgcg 60
cagcagagat tcaggcgcac gaccagaaag cacgtggctg agcttccagc cggacgttgt 120
ggccggagta aaaatccatc caaactttcc gcgatgctgg taaacctgtg gatgtcaatg 180
cctttgattt gaactaagca caggactacc tcgacgccgg cgccaacttt gtccgagtcg 240
gtgccgatgt ccagcaactc aacgctgctg gatacgaaaa gtgaaggaaa ataacgcatc 300
atgactatta atgtctccga actacttgcc aaagtcccca cgggtctact gattggtgat 360
tcctgggtgg aagcatccga gggcggtact ttcgatgtgg aaaacccagc gacgggtgaa 420
acaatcgcaa cgctcgcgtc tgctacttcc gaggatgcac tggctgctct tgatgctgca 480
tgcgctgttc aggccgagtg ggctaggacg ccagcgcgcg agcgttctaa tattttacga 540
cgcggtttcg agctcgtcgc ggaacgtgca gaagagttcg ccaccctcat gaccttggaa 600
atgggcaaac ctttggctga agctcgcggc gaagtcacct acggcaacga attcctgcgc 660
tggttctctg aggaagcagt ccgcctctac ggccgctacg gtgctacccc agaaggcaac 720
ctgcgcatga tgaccacccg caaaccagtt ggcccctgcc tgttgatcac cccatggaac 780
ttcccactag caatggccac ccgtaaggtt gcacccgcca tcgctgcagg ttgtgtcatg 840
gtgctcaagc cagctcgcct gaccccgctg acctcccagt attttgccca gaccatgctt 900
gatgccggtc ttccagcagg tgtcctcaat gtggtctccg gtgcttccgc ctctgcgatt 960
tccaacccga ttatggaaga cgatcgcctt cgtaaagtct cattcaccgg ctccacccca 1020
gttggccagc agctgctcaa aaaggctgcc gataaagttc tgcgcacctc catggaactc 1080
ggcggcaacg cacctttcat tgtcttcgag gacgccgacc tagatctcgc gatcgaaggt 1140
gccatgggcg caaaaatgcg caacatcggc gaagcttgca ccgcagccaa ccgtttccta 1200
gtccacgaat ccgtcgccga tgaattcggc cgacgcttcg cagcccgcct cgaggaacaa 1260
gtcctaggca acggcctcga cgaaggcgtc accgtaggcc cattggttga ggaaaaagca 1320
cgaaacagcg ttgcatcgct tgtcgacgcc gccgtctccg aaggtgccac cgtcctcacc 1380
ggtggcaagg ccggcacagg tgcaggctac ttctacgaac caacggtgct cacgggagtt 1440
tcaacagatg cagccatcct gaacgaagag atcttcggtc ccgtcgcacc gatcgtcacc 1500
ttctctgatg aagctgaagc tctgcgccta gccaattcca ccgaatacgg cctggcctcc 1560
tacgtgttca cccaagacac ctcacgcatc ttccgcgtct ccgacggcct cgagttcggc 1620
ctagtgggcg tcaactccgg tgtcatctct aacgccgctg caccttttgg tggcgtaaaa 1680
caatccggaa tgggccgcga aggtggtctc gaaggaattg aagagtacac ctccgtgcag 1740
tacatcggta tccgggatcc ttacgccggc taggttttgg cggatgagag aagattttca 1800
gcctgat 1807

<210> SEQ ID NO 43
<211> LENGTH: 1807
<212> TYPE: DNA
<213> ORGANISM: Artificial Sequence
<220> FEATURE:
<223> OTHER INFORMATION: Synthesized

<400> SEQUENCE: 43
gcttgcatgc ctgcaggtcg actctagagg atccccgtag tgctcgtcgt ggtaggtgcg 60
cagcagagat tcaggcgcac gaccagaaag cacgtggctg agcttccagc cggacgttgt 120

```
ggccggagta aaaatccatc caaactttcc gcgatgctgg taaacctgtg gatgtcaatg    180
cctttgattt gaactaagca caggactacc tcgacgccgg cgccaacttt gtccgagtcg    240
gtgccgatgt ccagcaactc aacgctgctg gatacgaaaa gtgaaggaaa ataacgcatc    300
atgactatta atgtctccga actacttgcc aaagtcccca cgggtctact gattggtgat    360
tcctgggtgg aagcatccga gggcggtact ttcgatgtgg aaaacccagc gacgggtgaa    420
acaatcgcaa cgctcgcgtc tgctacttcc gaggatgcac tggctgctct tgatgctgca    480
tgcgctgttc aggccgagtg ggctaggacg ccagcgcgcg agcgttctaa tattttacga    540
cgcggtttcg agctcgtcgc ggaacgtgca gaagagttcg ccaccctcat gaccttggaa    600
atgggcaaac ctttggctga agctcgcggc gaagtcacct acggcaacga attcctgcgc    660
tggttctctg aggaagcagt ccgcctctac ggccgctacg gtgctacccc agaaggcaac    720
ctgcgcatga tgaccacccg caaaccagtt ggcccctgcc tgttgatcac cccatggaac    780
ttcccactag caatggccac ccgtaaggtt gcacccgcca tcgctgcagg ttgtgtcatg    840
gtgctcaagc cagctcgcct gaccccgctg acctcccagt attttgccca gaccatactt    900
gatgccggtc ttccagcagg tgtcctcaat gtggtctccg gtgcttccgc ctctgcgatt    960
tccaacccga ttatggaaga cgatcgcctt cgtaaagtct cattcaccgg ctccacccca   1020
gttggccagc agctgctcaa aaaggctgcc gataaagttc tgcgcacctc catggaactc   1080
ggcggcaacg cacctttcat tgtcttcgag gacgccgacc tagatctcgc gatcgaaggt   1140
gccatgggcg caaaaaatgcg caacatcggc gaagcttgca ccgcagccaa ccgtttccta   1200
gtccacgaat ccgtcgccga tgaattcggc cgacgcttcg cagcccgcct cgaggaacaa   1260
gtcctaggca acggcctcga cgaaggcgtc accgtaggcc cattggttga ggaaaaagca   1320
cgaaacagcg ttgcatcgct tgtcgacgcc gccgtctccg aaggtgccac cgtcctcacc   1380
ggtggcaagg ccggcacagg tgcaggctac ttctacgaac caacggtgct cacgggagtt   1440
tcaacagatg cagccatcct gaacgaagag atcttcggtc ccgtcgcacc gatcgtcacc   1500
ttctctgatg aagctgaagc tctgcgccta gccaattcca ccgaatacgg cctggcctcc   1560
tacgtgttca cccaagacac ctcacgcatc ttccgcgtct ccgacggcct cgagttcggc   1620
ctagtgggcg tcaactccgg tgtcatctct aacgccgctg caccttttgg tggcgtaaaa   1680
caatccggaa tgggccgcga aggtggtctc gaaggaattg aagagtacac ctccgtgcag   1740
tacatcggta tccgggatcc ttacgccggc taggttttgg cggatgagag aagattttca   1800
gcctgat                                                             1807
```

<210> SEQ ID NO 44
<211> LENGTH: 1846
<212> TYPE: DNA
<213> ORGANISM: Artificial Sequence
<220> FEATURE:
<223> OTHER INFORMATION: Synthesized

<400> SEQUENCE: 44

```
agcggataac aatttcacac aggaaacaga attaattaag cttgcatgcc tgcaggtcga     60
ctctagagga tccccgtagt gctcgtcgtg gtaggtgcgc agcagagatt caggcgcacg    120
accagaaagc acgtggctga gcttccagcc ggacgttgtg gccggagtaa aaatccatcc    180
aaactttccg cgatgctggt aaacctgtgg atgtcaatgc ctttgatttg aactaagcac    240
aggactacct cgacgccggc gccaactttg tccgagtcgg tgccgatgtc cagcaactca    300
```

```
acgctgctgg atacgaaaag tgaaggaaaa taacgcatca tgactattaa tgtctccgaa    360

ctacttgcca aagtccccac gggtctactg attggtgatt cctgggtgga agcatccgag    420

ggcggtactt tcgatgtgga aaacccagcg acgggtgaaa caatcgcaac gctcgcgtct    480

gctacttccg aggatgcact ggctgctctt gatgctgcat gcgctgttca ggccgagtgg    540

gctaggacgc cagcgcgcga gcgttctaat attttacgac gcggtttcga gctcgtcgcg    600

gaacgtgcag aagagttcgc caccctcatg accttggaaa tgggcaaacc tttggctgaa    660

gctcgcggcg aagtcaccta cggcaacgaa ttcctgcgct ggttctctga ggaagcagtc    720

cgcctctacg gccgctacgg tgctacccca gaaggcaacc tgcgcatgat gaccacccgc    780

aaaccagttg gcccctgcct gttgatcacc ccatggaact tcccactagc aatggccacc    840

cgtaaggttg cacccgccat cgctgcaggt tgtgtcatgg tgctcaagcc agctcgcctg    900

accccgctga cctcccagta ttttgcccag accatacttg atgccggtct tccagcaggt    960

gtcctcaatg tggtctccgg tgcttccgcc tctgcgattt ccaacccgat tatggaagac   1020

gatcgccttc gtaaagtctc attcaccggc tccaccccag ttggccagca gctgctcaaa   1080

aaggctgccg ataaagttct gcgcacctcc atggaactcg gcggcaacgc acctttcatt   1140

gtcttcgagg acgccgacct agatctcgcg atcgaaggtg ccatgggcgc aaaaaatgcgc  1200

aacatcggcg aagcttgcac cgcagccaac cgtttcctag tccacgaatc cgtcgccgat   1260

gaattcggcc gacgcttcgc agcccgcctc gaggaacaag tcctaggcaa cggcctcgac   1320

gaaggcgtca ccgtaggccc attggttgag gaaaaagcac gaaacagcgt tgcatcgctt   1380

gtcgacgccg ccgtctccga aggtgccacc gtcctcaccg gtggcaaggc cggcacaggt   1440

gcaggctact tctacgaacc aacggtgctc acgggagttt caacagatgc agccatcctg   1500

aacgaagaga tcttcggtcc cgtcgcaccg atcgtcacct tctctgatga agctgaagct   1560

ctgcgcctag ccaattccac cgaatacggc ctggcctcct acgtgttcac ccaagacacc   1620

tcacgcatct tccgcgtctc cgacggcctc gagttcggcc tagtgggcgt caactccggt   1680

gtcatctcta acgccgctgc accttttggt ggcgtaaaac aatccggaat gggccgcgaa   1740

ggtggtctcg aaggaattga agagtacacc tccgtgcagt acatcggtat ccgggatcct   1800

tacgccggct aggttttggc ggatgagaga agattttcag cctgat                  1846
```

```
<210> SEQ ID NO 45
<211> LENGTH: 709
<212> TYPE: DNA
<213> ORGANISM: Artificial Sequence
<220> FEATURE:
<223> OTHER INFORMATION: Synthesized

<400> SEQUENCE: 45

cagtgccaag cttgcatgcc tgcaggtcga ctctaggtct gggggtgagc gcggatctga     60

ggcggtgacg tattaccagt attcctgggg tcgggcgcgt cgtagtttac gaggaatgga    120

ggagcagatt gcaaaagctg agcgtgcggt agccggcctc gttccggtca agcgttatcg    180

gtatgttgat cttaaagctg cacaaaagca ggtcaaccat gcattagcag ataagtatcg    240

ggcgttggct ggggtgaaag gatacgagac ctcacgcagt gatcttgctg ctggtgaggt    300

tattggggca tatcgtcagt tgtttaaaat tgagaaggcg tttcggatgg cgaagtcgga    360

tttgaaggct tgtccgattt ttcatcggaa gaaggattcg attgatgcgc atttaacgat    420

tgtgatggta tcgatggctg tggggcatgt gttggaacag cggtcggggt tgtcgttgaa    480

gcggttggtg cggatattga agagataccg cactttcact gtggaggtgg ctggccacag    540
```

ggttttcgct caggctccgg ttcctgatga tgttgcgtta attgttgatc ggttacctaa 600
accgtcagac taaaatggcc taagtcaggc aaaacacaaa aaatccacca caaacatccc 660
agtgtttgcg gtggatttgt aaaggggcag atggatgcgt tattttcct 709

<210> SEQ ID NO 46
<211> LENGTH: 734
<212> TYPE: DNA
<213> ORGANISM: Artificial Sequence
<220> FEATURE:
<223> OTHER INFORMATION: Synthesized

<400> SEQUENCE: 46
tggatttgta aaggggcaga tggatgcgtt attttccttc acttttcgta tccagcagcg 60
ttgagttgct ggacatcggc accgactcgg acaaagttgg cgccggcgtc gaggtagtcc 120
tgtgcttagt tcaaatcaaa ggcattgaca tccacaggtt taccagcatc gcggaaagtt 180
tggatggatt tttactccgg ccacaacgtc cggctggaag ctcagccacg tgctttctgg 240
tcgtgcgcct gaatctctgc tgcgcaccta ccacgacgag cactacccag ctgcggcaaa 300
cctcattgct ttcgataagg gatggtccac cctcatggtc cctcagctgg aagatccaga 360
ggctgtggag aggtactacg ttgctgcgga ggaattcacc gccggattcc tcaccgaaaa 420
ccaggacaat ctgatcactg cgggcacgga gcaccaggcg ctcgcgagcg gcttcccggt 480
ggggcgtcgc ttcaagtccg atattgcttt acgacgctgc gatgcggtga ccacccacat 540
cggccacgaa cactccgccg atggtcgatg gaagaaagcg aagactcacc actcaaccgc 600
ttcaccccag aagacggcga ccgcaacgca gtcttcgata tcaaggccat ctaccagcag 660
cattaccact ccttcgacct gttcgatgcg ccagaggggt accgagctcg aattcgtaat 720
catggtcata gctg 734

<210> SEQ ID NO 47
<211> LENGTH: 1405
<212> TYPE: DNA
<213> ORGANISM: Artificial Sequence
<220> FEATURE:
<223> OTHER INFORMATION: Synthesized

<400> SEQUENCE: 47
cagtgccaag cttgcatgcc tgcaggtcga ctctaggtct gggggtgagc gcggatctga 60
ggcggtgacg tattaccagt attcctgggg tcgggcgcgt cgtagtttac gaggaatgga 120
ggagcagatt gcaaaagctg agcgtgcggt agccggcctc gttccggtca agcgttatcg 180
gtatgttgat cttaaagctg cacaaaagca ggtcaaccat gcattagcag ataagtatcg 240
ggcgttggct ggggtgaaag gatacgagac ctcacgcagt gatcttgctg ctggtgaggt 300
tattggggca tatcgtcagt tgtttaaaat tgagaaggcg tttcggatgg cgaagtcgga 360
tttgaaggct tgtccgattt ttcatcggaa gaaggattcg attgatgcgc atttaacgat 420
tgtgatggta tcgatggctg tggggcatgt gttggaacag cggtcggggt tgtcgttgaa 480
gcggttggtg cggatattga agagataccg cactttcact gtggaggtgg ctggccacag 540
ggttttcgct caggctccgg ttcctgatga tgttgcgtta attgttgatc ggttacctaa 600
accgtcagac taaaatggcc taagtcaggc aaaacacaaa aaatccacca caaacatccc 660
agtgtttgcg gtggatttgt aaaggggcag atggatgcgt tattttcctt cacttttcgt 720
atccagcagc gttgagttgc tggacatcgg caccgactcg gacaaagttg gcgccggcgt 780
cgaggtagtc ctgtgcttag ttcaaatcaa aggcattgac atccacaggt ttaccagcat 840
cgcggaaagt ttggatggat ttttactccg gccacaacgt ccggctggaa gctcagccac 900
gtgctttctg gtcgtgcgcc tgaatctctg ctgcgcacct accacgacga gcactaccca 960
gctgcggcaa acctcattgc tttcgataag ggatggtcca ccctcatggt ccctcagctg 1020
gaagatccag aggctgtgga gaggtactac gttgctgcgg aggaattcac cgccggattc 1080
ctcaccgaaa accaggacaa tctgatcact gcgggcacgg agcaccaggc gctcgcgagc 1140
ggcttcccgg tggggcgtcg cttcaagtcc gatattgctt tacgacgctg cgatgcggtg 1200
accacccaca tcggccacga acactccgcc gatggtcgat ggaagaaagc gaagactcac 1260
cactcaaccg cttcacccca gaagacggcg accgcaacgc agtcttcgat atcaaggcca 1320
tctaccagca gcattaccac tccttcgacc tgttcgatgc gccagagggg taccgagctc 1380
gaattcgtaa tcatggtcat agctg 1405

<210> SEQ ID NO 48
<211> LENGTH: 2804
<212> TYPE: DNA
<213> ORGANISM: Artificial Sequence
<220> FEATURE:
<223> OTHER INFORMATION: Synthesized

<400> SEQUENCE: 48 gtctggggt gagcgcggat ctgaggcggt gacgtattac cagtattcct ggggtcgggc 60
gcgtcgtagt ttacgaggaa tggaggagca gattgcaaaa gctgagcgtg cggtagccgg 120
cctcgttccg gtcaagcgtt atcggtatgt tgatcttaaa gctgcacaaa agcaggtcaa 180
ccatgcatta gcagataagt atcgggcgtt ggctggggtg aaaggatacg agacctcacg 240
cagtgatctt gctgctggtg aggttattgg ggcatatcgt cagttgttta aaattgagaa 300
ggcgtttcgg atggcgaagt cggatttgaa ggcttgtccg atttttcatc ggaagaagga 360
ttcgattgat gcgcatttaa cgattgtgat ggtatcgatg gctgtggggc atgtgttgga 420
acagcggtcg gggttgtcgt tgaagcggtt ggtgcggata ttgaagagat accgcacttt 480
cactgtggag gtggctggcc acagggtttt cgctcaggct ccggttcctg atgatgttgc 540
gttaattgtt gatcggttac ctaaaccgtc agactaaaat ggcctaagtc aggcaaaaca 600
caaaaaatcc accacaaaca tcccagtgtt tgcggtggat ttgtaaaggg gcagatgcta 660
gccggcgtaa ggatcccgga taccgatgta ctgcacggag gtgtactctt caattccttc 720
gagaccacct tcgcggccca ttccggattg ttttacgcca ccaaaaggtg cagcggcgtt 780
agagatgaca ccggagttga cgcccactag gccgaactcg aggccgtcgg agacgcggaa 840
gatgcgtgag gtgtcttggg tgaacacgta ggaggccagg ccgtattcgg tggaattggc 900
taggcgcaga gcttcagctt catcagagaa ggtgacgatc ggtgcgacgg gaccgaagat 960
ctcttcgttc aggatggctg catctgttga aactcccgtg agcaccgttg gttcgtagaa 1020
gtagcctgca cctgtgccgg ccttgccacc ggtgaggacg gtggcacctt cggagacggc 1080
ggcgtcgaca agcgatgcaa cgctgtttcg tgctttttcc tcaaccaatg ggcctacggt 1140
gacgccttcg tcgaggccgt tgcctaggac ttgttcctcg aggcgggctg cgaagcgtcg 1200
gccgaattca tcggcgacgg attcgtggac taggaaacgg ttggctgcgg tgcaagcttc 1260
gccgatgttg cgcatttttg cgcccatggc accttcgatc gcgagatcta ggtcggcgtc 1320
ctcgaagaca atgaaaggtg cgttgccgcc gagttccatg gaggtgcgca gaactttatc 1380
ggcagccttt ttgagcagct gctggccaac tggggtggag ccggtgaatg agactttacg 1440

```
aaggcgatcg tcttccataa tcgggttgga aatcgcagag gcggaagcac cggagaccac   1500
attgaggaca cctgctggaa gaccggcatc aagcatggtc tgggcaaaat actgggaggt   1560
cagcggggtc aggcgagctg gcttgagcac catgacacaa cctgcagcga tggcgggtgc   1620
aaccttacgg gtggccattg ctagtgggaa gttccatggg gtgatcaaca ggcaggggcc   1680
aactggtttg cgggtggtca tcatgcgcag gttgccttct ggggtagcac cgtagcggcc   1740
gtagaggcgg actgcttcct cagagaacca gcgcaggaat tcgttgccgt aggtgacttc   1800
gccgcgagct tcagccaaag gtttgcccat ttccaaggtc atgagggtgg cgaactcttc   1860
tgcacgttcc gcgacgagct cgaaaccgcg tcgtaaaata ttagaacgct cgcgcgctgg   1920
cgtcctagcc cactcggcct gaacagcgca tgcagcatca agagcagcca gtgcatcctc   1980
ggaagtagca gacgcgagcg ttgcgattgt ttcacccgtc gctgggtttt ccacatcgaa   2040
agtaccgccc tcggatgctt ccacccagga atcaccaatc agtagacccg tggggacttt   2100
ggcaagtagt tcggagacat taatagtcat gatgcgttat tttccttcac ttttcgtatc   2160
cagcagcgtt gagttgctgg acatcggcac cgactcggac aaagttggcg ccggcgtcga   2220
ggtagtcctg tgcttagttc aaatcaaagg cattgacatc cacaggttta ccagcatcgc   2280
ggaaagtttg gatggatttt tactccggcc acaacgtccg gctggaagct cagccacgtg   2340
ctttctggtc gtgcgcctga atctctgctg cgcacctacc acgacgagca ctacccagct   2400
gcggcaaacc tcattgcttt cgataaggga tggtccaccc tcatggtccc tcagctggaa   2460
gatccagagg ctgtggagag gtactacgtt gctgcggagg aattcaccgc cggattcctc   2520
accgaaaacc aggacaatct gatcactgcg ggcacggagc accaggcgct cgcgagcggc   2580
ttcccggtgg ggcgtcgctt caagtccgat attgctttac gacgctgcga tgcggtgacc   2640
acccacatcg gccacgaaca ctccgccgat ggtcgatgga agaaagcgaa gactcaccac   2700
tcaaccgctt caccccagaa gacggcgacc gcaacgcagt cttcgatatc aaggccatct   2760
accagcagca ttaccactcc ttcgacctgt tcgatgcgcc agac                    2804
```

<210> SEQ ID NO 49
<211> LENGTH: 1331
<212> TYPE: DNA
<213> ORGANISM: Artificial Sequence
<220> FEATURE:
<223> OTHER INFORMATION: Synthesized

<400> SEQUENCE: 49

```
gtctgggggt gagcgcggat ctgaggcggt gacgtattac cagtattcct ggggtcgggc     60
gcgtcgtagt ttacgaggaa tggaggagca gattgcaaaa gctgagcgtg cggtagccgg    120
cctcgttccg gtcaagcgtt atcggtatgt tgatcttaaa gctgcacaaa agcaggtcaa    180
ccatgcatta gcagataagt atcgggcgtt ggctggggtg aaaggatacg agacctcacg    240
cagtgatctt gctgctggtg aggttattgg ggcatatcgt cagttgttta aaattgagaa    300
ggcgtttcgg atggcgaagt cggatttgaa ggcttgtccg atttttcatc ggaagaagga    360
ttcgattgat gcgcatttaa cgattgtgat ggtatcgatg gctgtggggc atgtgttgga    420
acagcggtcg gggttgtcgt tgaagcggtt ggtgcggata ttgaagagat accgcacttt    480
cactgtggag gtggctggcc acagggtttt cgctcaggct ccggttcctg atgatgttgc    540
gttaattgtt gatcggttac ctaaaccgtc agactaaaat ggcctaagtc aggcaaaaca    600
caaaaaatcc accacaaaca tcccagtgtt tgcggtggat ttgtaaaggg gcagatggat    660
```

-continued

```
gcgttatttt ccttcacttt tcgtatccag cagcgttgag ttgctggaca tcggcaccga    720
ctcggacaaa gttggcgccg gcgtcgaggt agtcctgtgc ttagttcaaa tcaaaggcat    780
tgacatccac aggtttacca gcatcgcgga aagtttggat ggatttttac tccggccaca    840
acgtccggct ggaagctcag ccacgtgctt tctggtcgtg cgcctgaatc tctgctgcgc    900
acctaccacg acgagcacta cccagctgcg gcaaacctca ttgctttcga taagggatgg    960
tccaccctca tggtccctca gctggaagat ccagaggctg tggagaggta ctacgttgct   1020
gcggaggaat tcaccgccgg attcctcacc gaaaaccagg acaatctgat cactgcgggc   1080
acggagcacc aggcgctcgc gagcggcttc ccggtggggc gtcgcttcaa gtccgatatt   1140
gctttacgac gctgcgatgc ggtgaccacc cacatcggcc acgaacactc cgccgatggt   1200
cgatggaaga aagcgaagac tcaccactca accgcttcac cccagaagac ggcgaccgca   1260
acgcagtctt cgatatcaag gccatctacc agcagcatta ccactccttc gacctgttcg   1320
atgcgccaga g                                                        1331
```

STRAIN HAVING ENHANCED L-GLUTAMIC ACID PRODUCTIVITY, CONSTRUCTION METHOD THEREFOR AND APPLICATION THEREOF

CROSS-REFERENCE TO RELATED APPLICATION

This application is a 371 of international application of PCT application serial no. PCT/CN2021/142440, filed on Dec. 29, 2021, which claims the priority benefit of China application no. 202011631311.X, filed on Dec. 30, 2020. The entirety of each of the above mentioned patent applications is hereby incorporated by reference herein and made a part of this specification.

TECHNICAL FIELD

The present invention belongs to the technical field of gene engineering and microorganisms, and in particular relates to strain having enhanced L-glutamic acid production capacity, and method for constructing the same and use thereof.

BACKGROUND

L-glutamic acid has a chemical name: L-2-aminoglutaric acid; a molecular formula: $C_5H_9O_4N$; and a molecular weight: 147.13. L-glutamic acid is a nonessential amino acid. Glutamic acid existing in biological organisms belongs to L-type glutamic acid, and L-glutamic acid is a precursor of monosodium glutamate. After being eaten, monosodium glutamate can also be converted into glutamic acid in the stomach, then digested and absorbed to participate in the synthesis of protein, and other amino acids can be synthesized by transamination, which has a high value in nutrition. Apart from a wide range of applications in foods, it is also applied to medicine, cosmetics and agricultural production. Glutamate has the highest content in brain among the major organs of human body, and meanwhile glutamic acid is the only amino acid involved in the metabolism in human brain, which plays an important role in maintaining the function of nervous system. Therefore, for those suffering from neurasthenia, increasing glutamic acid intake can improve the function of nervous system. In cosmetic industry, glutamic acid can be used to synthesize sodium polyglutamate. Because of its strong hygroscopicity, it can be used as an emollient. Glutamic acid can also be combined with lauroyl chloride to generate sodium lauroyl glutamate, which is widely used in cosmetic industry. Glutamic acid mainly serves to produce bactericidal agents such as glutamate ketone in agriculture. In the process of fertilization, glutamic acid can also be used as a carrier of fertilizer to promote the absorption of nitrogen, phosphorus and potassium by crops.

In 1956, a glutamic acid-producing bacterium, *Corynebacterium glutamicum*, was isolated from nature, a major change in the history of monosodium glutamate production. In 1957, the era of producing monosodium glutamate by fermentation began. The success of glutamic acid production by fermentation is a great pioneering work of the whole fermentation industry, and it also greatly promotes the research and production of other fermented products. For industrial fermentation, the main factors that determine the level of fermentation production are strain performance, fermentation process, and downstream extraction process, etc. Among these factors, the acid production level of strains is the internal cause, a key to determine the success or failure of fermentation. Breeding of excellent strains is still the key to high-yield L-glutamic acid. With the progress in high-throughput screening technology, combined with traditional mutagenesis technology, it is helpful to find out high-yield L-glutamic acid mutant strains with unknown traits. These mutant strains may change the activity of a certain point in the metabolic pathway of L-glutamic acid or the recombination and integration along the whole pathway, so as to improve the acid production.

Although some strains that can increase the production of L-glutamic acid have been screened, more mutant strains for producing L-glutamic acid in high yield need to be found in order to meet the increasing demand.

SUMMARY

Aiming at the shortcomings of the prior art, the present invention provides a polynucleotide and a recombinant strain comprising the polynucleotide, and uses the recombinant strain to improve the L-glutamic acid production capacity of a bacterium. In order to achieve the above goals, the inventors of the present invention have found in research that the BBD29_00405 gene (GenBank: ANU32350.1) in the genome of *Corynebacterium glutamicum* ATCC13869 (GenBank: CP016335.1) having L-glutamic acid production capacity can be modified, or improved with respect to its expression to provide a recombinant strain with an increased production of L-glutamic acid. Compared with a wild-type strain that has not been modified, the capacity of the recombinant strain for producing L-glutamic acid is higher.

The present invention is implemented with the technical solutions as follows:

A first aspect of the present invention provides a bacterium for generating L-glutamic acid, having an improved expression of a polynucleotide encoding an amino acid sequence as set forth in SEQ ID NO: 3. According to the present invention, the improved expression is an enhanced expression of the polynucleotide, or having a point mutation in the polynucleotide encoding an amino acid sequence of SEQ ID NO: 3, or having a point mutation in, and an enhanced expression of the polynucleotide encoding an amino acid sequence of SEQ ID NO: 3.

The amino acid sequence of SEQ ID NO: 3 is a protein coded by the gene BBD29_00405.

The bacterium has an enhanced L-glutamic acid production capacity compared with an unmodified strain.

In the present invention, the term "bacterium having L-glutamic acid production capacity" refers to a bacterium having such a capacity of producing and accumulating target L-glutamic acid in a culture medium and/or in a cell of the bacterium that L-glutamic acid can be collected when the bacterium is cultured in the culture medium. A bacterium having L-glutamic acid production capacity can be a bacterium capable of accumulating target L-glutamic acid in a culture medium and/or in a cell of the bacterium in an amount greater than that with an unmodified strain.

The term "unmodified strain" refers to a control strain which has not been modified in a manner such that a specific feature is incorporated. That is, examples of the unmodified strain comprise a wild-type strain and a parent strain.

In the present invention, the term "L-glutamic acid" refers to L-glutamic acid in a free form, a salt thereof or a mixture thereof, unless otherwise specified.

The polynucleotide can encode an amino acid sequence having about 90% or more, about 92% or more, about 95% or more, about 97% or more, about 98% or more, or about 99% or more sequence homology with an amino acid sequence of SEQ ID NO: 3. As used herein, the term "homology" refers to percentage identity between two polynucleotides or two polypeptides as modules. Sequence homology can be measured between one module and another module using a method known in the art. For example, such sequence homology can be measured by virtue of BLAST algorithm.

The expression of a polynucleotide can be enhanced: by substituting or mutating an expression regulatory sequence, introducing a mutation to the sequence of the polynucleotide, and by increasing the copy number of the polynucleotide inserted via a chromosome or introduced with a vector, or a combination thereof, etc.

The expression regulatory sequence of a polynucleotide can be modified. The expression regulatory sequence controls the expression of a polynucleotide operably linked thereto, and can comprise, for example, promoters, terminators, enhancers, silencers and the like. A polynucleotide can have a change in an initiation codon. A polynucleotide can be incorporated into a specific site of a chromosome, thereby increasing copy number. Herein, a specific site can comprise, for example, a transposon site or an intergenic site. In addition, a polynucleotide can be incorporated into an expression vector, and the expression vector is introduced into a host cell, thus increasing copy number.

In an embodiment of the present invention, a polynucleotide, or a polynucleotide having a point mutation is incorporated into a specific site of a chromosome of a microorganism, thus increasing copy number.

In an embodiment of the present invention, a polynucleotide with a promoter sequence, or a polynucleotide having a point mutation with a promoter sequence is incorporated into a specific site of a chromosome of a microorganism, thus overexpressing the nucleic sequence.

In an embodiment of the present invention, a polynucleotide, or a polynucleotide having a point mutation is incorporated into an expression vector, and the expression vector is introduced into a host cell, thus increasing copy number.

In an embodiment of the present invention, a polynucleotide with a promoter sequence, or a polynucleotide having a point mutation with a promoter sequence is incorporated into an expression vector, and the expression vector is introduced into a host cell, thus overexpressing the amino acid sequence.

In a specific embodiment of the present invention, the polynucleotide can comprise a nucleotide sequence of SEQ ID NO: 1.

In an embodiment of the present invention, the polynucleotide encoding an amino acid sequence of SEQ ID NO: 3 has a point mutation such that methionine at position 199 in the amino acid sequence of SEQ ID NO: 3 is substituted with a different amino acid.

According to the present invention, preferably methionine at position 199 is substituted with isoleucine.

According to the present invention, as set forth in SEQ ID NO: 4 is the amino acid sequence following substitution with isoleucine of methionine at position 199 in an amino acid sequence set forth in SEQ ID NO: 3.

In an embodiment of the present invention, the polynucleotide sequence having a point mutation is formed from a mutation to the base at position 597 of a polynucleotide sequence set forth in SEQ ID NO: 1.

According to the present invention, the mutation comprises a mutation of the base at position 597 of a polynucleotide sequence set forth in SEQ ID NO: 1 from guanine (G) to adenine (A).

In an embodiment of the present invention, the polynucleotide sequence having a point mutation comprises a polynucleotide sequence set forth in SEQ ID NO: 2.

As used herein, the term "operably linked" refers to a functional link between a regulatory sequence and a polynucleotide sequence, whereby the regulatory sequence controls transcription and/or translation of the polynucleotide sequence. A regulatory sequence can be a strong promoter which can enhance the expression level of a polynucleotide. A regulatory sequence can be a promoter derived from a microorganism belonging to the genus *Corynebacterium* or can be a promoter derived from other microorganisms. For example, the promoter can be trc promoter, gap promoter, tac promoter, T7 promoter, lac promoter, trp promoter, araBAD promoter or cj7 promoter.

In a specific embodiment of the present invention, the promoter is a promoter of a polynucleotide encoding an amino acid sequence of SEQ ID NO: 3 (BBD29_00405).

As used herein, the term "vector" refers to a polynucleotide construct containing a regulatory sequence of a gene and a gene sequence and configured to express a target gene in a suitable host cell. Or, a vector can also refer to a polynucleotide construct containing a sequence for homologous recombination such that due to the vector introduced into a host cell, the regulatory sequence of an endogenous gene in the genome of the host cell can be changed, or a target gene that can be expressed can be inserted into a specific site of the genome of a host. In this regard, the vector used in the present invention can further comprise a selective marker to determine the introduction of the vector into a host cell or the insertion of the vector into the chromosome of a host cell. A selective marker can comprise a marker providing a selectable phenotype, such as drug resistance, auxotroph, resistance to cytotoxic agents, or expression of a surface protein. In an environment treated with such a selective agent, the transformed cell can be selected since only the cell that expresses the selective marker can survive or display different phenotypic traits. The vector as described herein is well known to those skilled in the art, including but not limited to: plasmid, bacteriophage (such as λ bacteriophage or M13 filamentous bacteriophage etc.), cosmid (i.e., Cosmid) or viral vector.

In some specific embodiments of the present invention, the vector used is pK18mobsacB plasmid, and pXMJ19 plasmid.

As used herein, the term "transformation" refers to introduction of a polynucleotide into a host cell, such that the polynucleotide can be replication-competent as an element foreign to a genome or by being inserted into the genome of a host cell. A method for transforming the vector used in the present invention can comprise a method for introducing a nucleic acid into a cell. In addition, as disclosed in the related techniques, a method with electric pulse can be performed according to a host cell.

Herein, the microorganism can be yeast, bacterium, alga or fungi.

According to the present invention, the bacterium can be a microorganism belonging to the genus *Corynebacterium*, such as *Corynebacterium acetoacidophilum*, *Corynebacterium acetoglutamicum*, *Corynebacterium callunae*, *Corynebacterium glutamicum*, *Brevibacterium flavum*, *Brevibacterium lactofermentum*, *Corynebacterium ammoniagenes*, *Corynebacterium pekinense*, *Brevibacterium saccharolyticum*, *Brevibacterium roseum*, and *Brevibacterium thiogenitalis*, etc.

In an implementation of the present invention, the microorganism belonging to the genus *Corynebacterium* is *Corynebacterium glutamicum* ATCC13869.

In an implementation of the present invention, the microorganism belonging to the genus *Corynebacterium* is *Corynebacterium glutamicum* YPGLU001, and has been deposited at China General Microbiological Culture Collection Center, abbreviated as CGMCC, Address: No. 3, Yard 1, Beichen West Road, Chaoyang District, Beijing, Post Code: 100101 on Nov. 23, 2020, with Accession Number of the Biological Deposit: CGMCC No. 21220.

A second aspect of the present invention provides a polynucleotide sequence, an amino acid sequence coded by the polynucleotide sequence, a recombinant vector comprising the polynucleotide sequence, and a recombinant strain containing the polynucleotide sequence.

According to the present invention, the polynucleotide sequence comprises a polynucleotide encoding a polypeptide containing an amino acid sequence set forth in SEQ ID NO: 3 with methionine at position 199 in the sequence substituted with a different amino acid.

According to the present invention, preferably methionine at position 199 is substituted with isoleucine.

According to the present invention, as set forth in SEQ ID NO: 4 is the amino acid sequence following substitution with isoleucine of methionine at position 199 in an amino acid sequence set forth in SEQ ID NO: 3.

According to the present invention, preferably the polynucleotide sequence encoding a polypeptide containing an amino acid sequence set forth in SEQ ID NO: 3 contains a polynucleotide sequence as set forth in SEQ ID NO: 1.

In an embodiment of the present invention, the polynucleotide sequence is formed from a mutation to the base at position 597 in a polynucleotide sequence set forth in SEQ ID NO: 1.

According to the present invention, the mutation refers to a change in the base/nucleotide of the site, and the method for mutation can be at least one selected from mutagenesis, PCR site-directed mutation, and/or homologous recombination, etc. In the present invention, PCR site-directed mutation and/or homologous recombination are preferably used.

According to the present invention, the mutation comprises a mutation at position 597 in a polynucleotide sequence set forth in SEQ ID NO: 1 from guanine (G) to adenine (A).

In an embodiment of the present invention, the polynucleotide sequence comprises a polynucleotide sequence set forth in SEQ ID NO: 2.

According to the present invention, the amino acid sequence comprises an amino acid sequence set forth in SEQ ID NO: 4.

According to the present invention, the recombinant vector is constructed by introducing the polynucleotide sequence to a plasmid.

In an embodiment of the present invention, the plasmid is pK18mobsacB plasmid.

In another embodiment of the present invention, the plasmid is pXMJ19 plasmid.

Specifically, the polynucleotide sequence and the plasmid can be constructed as a recombinant vector by virtue of NEBuider recombination system.

According to the present invention, the recombinant strain contains the polynucleotide sequence.

As an implementation of the present invention, a starting strain of the recombinant strain is *Corynebacterium glutamicum* YPGLU001 with Accession Number of the Biological Deposit: CGMCC No. 21220.

As an implementation of the present invention, a starting strain of the recombinant strain is ATCC 13869.

A third aspect of the present invention provides use of the polynucleotide sequence, an amino acid sequence coded by the polynucleotide sequence, a recombinant vector comprising the polynucleotide sequence, and a recombinant strain containing the polynucleotide sequence in the production of L-glutamic acid.

A fourth aspect of the present invention further provides a method for constructing a recombinant strain generating L-glutamic acid.

According to the present invention, the method for constructing comprises the step of:

engineering a polynucleotide sequence of a wild-type BBD29_00405 gene as set forth in SEQ ID NO: 1 in a host strain to cause a mutation to the base at position 597 to provide a recombinant strain containing a mutated BBD29_00405 coding gene.

According to the method for constructing of the present invention, the engineering comprises at least one of mutagenesis, PCR site-directed mutation, and/or homologous recombination, etc.

According to the method for constructing of the present invention, the mutation refers to a change of the base at position 597 in SEQ ID NO: 1 from guanine (G) to adenine (A); specifically, the polynucleotide sequence containing a mutated BBD29_00405 coding gene is set forth in SEQ ID NO: 2.

Further, the method for constructing comprises the steps of:

(1) engineering a nucleotide sequence of a wild-type BBD29_00405 gene as set forth in SEQ ID NO: 1 to cause a mutation to the base at position 597 to provide a mutated BBD29_00405 gene polynucleotide sequence;

(2) linking the mutated polynucleotide sequence to a plasmid to construct a recombinant vector;

(3) introducing the recombinant vector into a host strain to provide a recombinant strain containing a mutated BBD29_00405 coding gene.

According to the method for constructing of the present invention, the step (1) comprises constructing a BBD29_00405 gene with a point mutation: according to a genome sequence of an unmodified strain, synthesizing two pairs of primers P1, P2 and P3, P4 for amplifying a fragment of the BBD29_00405 gene, and introducing a point mutation to a wild-type BBD29_00405 gene, SEQ ID NO: 1, by virtue of PCR site-directed mutation to provide a BBD29_00405 gene nucleotide sequence with a point mutation, SEQ ID NO: 2, designated as BBD29_00405$^{G597A}$.

In an embodiment of the present invention, the genome of the unmodified strain can be derived from the strain ATCC13869, and its genome sequence GenBank: CP016335.1 can be available from the NCBI website.

In an implementation of the present invention, in the step (1), the primers are:

```
P1:
                                         (SEQ ID NO: 5)
5'CAGTGCCAAGCTTGCATGCCTGCAGGTCGACTCTAGATGACTATTAAT
GTCTCCGA 3'
```

-continued

P2:

(SEQ ID NO: 6)
5'AGACCGGCATCAAGTATGGTCTGGGCA3'

P3:

(SEQ ID NO: 7)
5'TGCCCAGACCATACTTGATGCCGGTCT3'

P4:

(SEQ ID NO: 8)
5'CAGCTATGACCATGATTACGAATTCGAGCTCGGTACCCCTAGCCGGCG

TAAGGATCCCGGAT3'

In an implementation of the present invention, the PCR amplification is performed in the following manner: pre-denaturation for 5 min at 94° C., denaturation for 30 s at 94° C., annealing for 30 s at 52° C., and extension for 40 s at 72° C. (30 circles), and overextension for 10 min at 72° C.

In an implementation of the present invention, the overlap PCR amplification is performed in the following manner: pre-denaturation for 5 min at 94° C., denaturation for 30 s at 94° C., annealing for 30 s at 52° C., and extension for 100 s at 72° C. (30 circles), and overextension for 10 min at 72° C.

According to the method for constructing of the present invention, the step (2) comprises constructing a recombinant plasmid, comprising assembling an isolated and purified BBD29_00405$^{G597A}$ with pK18mobsacB plasmid by virtue of NEBuider recombination system to provide a recombinant plasmid.

According to the method for constructing of the present invention, the step (3) comprises constructing a recombinant strain by transforming a recombinant plasmid to a host strain to provide a recombinant strain.

In an implementation of the present invention, the transforming in the step (3) is by an electrotransformation method.

In an embodiment of the present invention, the host strain is ATCC 13869.

In an embodiment of the present invention, the host strain is *Corynebacterium glutamicum* YPGLU001 with Accession Number of the Biological Deposit: CGMCC No. 21220.

In an embodiment of the present invention, the recombination is achieved by homologous recombination.

A fifth aspect of the present invention further provides a method for constructing a recombinant strain generating L-glutamic acid.

According to the present invention, the method for constructing comprises the step of:

amplifying upstream and downstream homology arm fragments of BBD29_00405 and a sequence of a BBD29_00405 gene coding region and a promoter region thereof, and introducing BBD29_00405 or BBD29_00405$^{G597A}$ gene into the genome of a host strain in a manner of homologous recombination so as to enable the strain to overexpress the BBD29_00405 or BBD29_00405$^{G597A}$ gene.

In an embodiment of the present invention, the primers for amplifying the upstream homology arm fragments are:

P7:
5'CAGTGCCAAGCTTGCATGCCTGCAGGTCGACTCTAGGACCCGCTTGCC

ATACGAAG 3'

P8:
5'CCTACCACGA CGAGCACTAC ATCTACTCAT CTGAAGAATC 3'

In an embodiment of the present invention, the primers for amplifying the downstream homologous arm fragments are:

P11:
5'GGGATCCTTA CGCCGGCTAG TTCGTGGGCA CTCTGGTTTG 3'

P12:
5'CAGCTATGACCATGATTACGAATTCGAGCTCGGTACCCCATAAGAAAC

AACCACTTCC3'

In an embodiment of the present invention, the primers for amplifying the sequence of the gene coding region and the promoter region thereof are:

P9:

(SEQ ID NO: 13)
5'GATTCTTCAG ATGAGTAGAT GTAGTGCTCG TCGTGGTAGG 3'

P10:

SEQ ID NO: 14)
5'CAAACCAGAG TGCCCACGAA CTAGCCGGCG TAAGGATCCC 3'

In an embodiment of the present invention, with the above-mentioned P7/P12 as primers again, amplification is performed using as templates a mixture of three fragments, the amplified upstream homology arm fragment, downstream homology arm fragment, and fragment of the sequence of the gene coding region and the promoter region thereof, to provide an integrated homology arm fragment.

In an embodiment of the present invention, the PCR system used comprises: 10×Ex Taq Buffer 5 μL, dNTP Mixture (2.5 mM each) 4 μL, $Mg^{2+}$ (25 mM) 4 μL, primers (10 μM) 2 μL each, and Ex Taq (5 U/μL) 0.25 μL in a total volume of 50 μL; the PCR amplification is performed in the following manner: pre-denaturation for 5 min at 94° C., denaturation for 30 s at 94° C., annealing for 30 s at 52° C., and extension for 180 s at 72° C. (30 circles), and overextension for 10 min at 72° C.

In an embodiment of the present invention, NEBuider recombination system is used to assemble shuttle plasmid PK18mobsacB with the integrated homology arm fragment to provide an integrative plasmid.

In an embodiment of the present invention, a host strain is transfected with the integrative plasmid to introduce BBD29_00405 or BBD29_00405$^{G597A}$ gene into the genome of the host strain in a manner of homologous recombination.

In an embodiment of the present invention, the host strain is *Corynebacterium glutamicum* YPGLU001 with Accession Number of the Biological Deposit: CGMCC No. 21220.

In an embodiment of the present invention, the host strain is ATCC 13869.

In an embodiment of the present invention, the host strain is a strain bearing a polynucleotide sequence set forth in SEQ ID NO: 2.

A sixth aspect of the present invention further provides a method for constructing a recombinant strain producing L-glutamic acid.

According to the present invention, the method for constructing comprises the steps of:

amplifying the sequence of BBD29_00405 gene coding region and a promoter region, or the sequence of BBD29_00405$^{G597A}$ gene coding region and a promoter region, constructing an overexpression plasmid vector, and transforming the vector into a host strain to enable the strain to overexpress BBD29_00405 or BBD29_00405$^{G597A}$ gene.

In an embodiment of the present invention, the primers for amplifying the sequence of the gene coding region and the promoter region thereof are:

```
P17:
                                    (SEQ ID NO: 21)
5'GCTTGCATGCCTGCAGGTCGACTCTAGAGGATCCCCGTAGTGCTCGTC

GTGGTAGG 3'

P18:
                                    (SEQ ID NO: 22)
5'ATCAGGCTGAAAATCTTCTCTCATCCGCCAAAACCTAGCCGGCGTAAG

GATCCCGGAT 3'
```

In an embodiment of the present invention, the PCR system comprises: 10×Ex Taq Buffer 5 μL, dNTP Mixture (2.5 mM each) 4 μL, $Mg^{2+}$ (25 mM) 4 μL, primers (10 μM) 2 μL each, Ex Taq (5 U/μL) 0.25 μL, in a total volume of 50 μL. The PCR amplification is performed in the following manner: pre-denaturation for 5 min at 94° C., denaturation for 30 s at 94° C., annealing for 30 s at 52° C., extension for 100 s at 72° C. (30 circles), and overextension for 10 min at 72° C.

In an embodiment of the present invention, NEBuider recombination system is used to assemble shuttle plasmid pXMJ19 with BBD29_00405 or BBD29_00405$^{G597A}$ fragment having its own promoters to provide an overexpression plasmid.

In an embodiment of the present invention, the host strain is *Corynebacterium glutamicum* YPGLU001 with Accession Number of the Biological Deposit: CGMCC No. 21220.

In an embodiment of the present invention, the host strain is ATCC 13869.

In an embodiment of the present invention, the host strain is a strain bearing a polynucleotide sequence set forth in SEQ ID NO: 2.

The recombinant strain provided in the present invention can be individually applied to fermentation for producing L-glutamic acid, and can also be in hybrid fermentation with other L-glutamic acid-producing bacteria for producing L-glutamic acid.

Another aspect of the present invention provides a method for producing L-glutamic acid, the method comprising culturing the bacterium; and obtaining L-glutamic acid from a culture.

A bacterium can be cultured in a suitable culture medium under culturing conditions as known in the art. The culture medium can comprise: carbon source, nitrogen source, trace elements, and a combination thereof. In culturing, pH of the culture can be adjusted. In addition, bubbles can be prevented from generating in culturing, for example, by using a defoamer to prevent bubbles generation. Further, gases can be injected into the culture in culturing. The gases can comprise any ones capable of maintaining an aerobic condition for the culture. In culturing, the temperature of the culture can be from 20° C. to 45° C. The generated L-glutamic acid can be recovered from the culture, i.e., the culture is treated with sulfuric acid or hydrochloric acid, etc. followed by a combination of methods such as anion-exchange chromatography, condensation, crystallization, and isoelectric precipitation.

The present invention also provides a protein, designated as protein BBD29_00405$^{M199I}$ wherein the protein can be any one of:

A1) a protein whose amino acid sequence is SEQ ID NO: 4;

A2) a protein having 80% or more identity to and the same function as the protein indicated in A1), as obtained by subjecting the amino acid sequence set forth in SEQ ID NO: 4 to substitution and/or deletion and/or addition of amino acid residues;

A3) a fusion protein having the same function, as obtained by linking a tag to the N-terminus and/or C-terminus of A1) or A2).

The present invention also provides a nucleic acid molecule, designated as BBD29_00405$^{G597A}$, wherein the nucleic acid molecule BBD29_00405$^{G597A}$ can be any one of:

B1) a nucleic acid molecule encoding the protein BBD29_00405$^{M199I}$;

B2) a DNA molecule whose coding sequence is set forth in SEQ ID NO: 2;

B3) a DNA molecule whose nucleotide sequence is set forth in SEQ ID NO: 2.

The DNA molecule set forth in SEQ ID NO: 2 is the BBD29_00405$^{G597A}$ gene of the present invention.

The DNA molecule set forth in SEQ ID NO: 2 (the BBD29_00405$^{G597A}$ gene) encodes the protein BBD29_00405$^{M199I}$ set forth in SEQ ID NO: 4.

The amino acid sequence of the protein BBD29_00405$^{M199I}$ (SEQ ID NO: 4) is derived from a change of methionine (M) at position 199 of SEQ ID NO: 3 to isoleucine (I).

The present invention also provides a biomaterial, wherein the biomaterial can be any one of:

C1) an expression cassette comprising the nucleic acid molecule BBD29_00405$^{G597A}$;

C2) a recombinant vector comprising the nucleic acid molecule BBD29_00405$^{G597A}$ or a recombinant vector comprising the expression cassette of C1);

C3) a recombinant microorganism comprising the nucleic acid molecule BBD29_00405$^{G597A}$, or a recombinant microorganism comprising the expression cassette of C1), or a recombinant microorganism comprising the recombinant vector of C2).

The present invention also provides any one of the following uses of any one of D1)-D8):

F1) use of any one of D1)-D8) in the regulation of the production of L-glutamic acid of a microorganism;

F2) use of any one of D1)-D8) in the construction of a genetically engineered bacterium for producing L-glutamic acid;

F3) use of any one of D1)-D8) in the preparation of L-glutamic acid;

wherein the D1)-D8) is:

D1) the protein BBD29_00405$^{M199I}$.

D2) the nucleic acid molecule BBD29_00405$^{G597A}$;

D3) the biomaterial;

D4) a DNA molecule whose nucleotide sequence is SEQ ID NO: 1;

D5) a DNA molecule having 90% or more identity to and the same function as the DNA molecule set forth in SEQ ID NO: 1, as obtained by subjecting the nucleotide sequence set forth in SEQ ID NO: 1 to modification, and/or substitution and/or deletion and/or addition of one or several nucleotides;

D6) an expression cassette comprising the DNA molecule in D4) or D5);

D7) a recombinant vector comprising the DNA molecule in D4) or D5), or a recombinant vector comprising the expression cassette of D6);

D8) a recombinant microorganism comprising the DNA molecule in D4) or D5), or a recombinant microorganism comprising the expression cassette of D6), or a recombinant microorganism comprising the recombinant vector of D7).

The DNA molecule set forth in SEQ ID NO: 1 is the BBD29_00405 gene of the present invention.

The DNA molecule set forth in SEQ ID NO: 1 (the BBD29_00405 gene) encodes a protein set forth in SEQ ID NO: 3.

Herein, identity refers to the identity between amino acid sequences or nucleotide sequences. International homology retrieval sites on the Internet can be employed to determine the identity between amino acid sequences, such as the BLAST page on the NCBI homepage website. For example, in Advanced BLAST2.1, blastp can be used as a program, with the Expect value set at 10, each Filter set to OFF, BLOSUM62 used as Matrix, and Gap existence cost, Per residue gap cost and Lambda ratio set at 11, 1 and 0.85 (default values), respectively, and a search is done for the identity between a pair of amino acid sequences for calculation, and then a value of identity (%) can be available.

Herein, the 80% or more identity can be an identity of at least 80%, 81%, 82%, 83%, 84%, 85%, 86%, 87%, 88%, 89%, 90%, 91%, 92%, 93%, 94%, 95%, 96%, 97%, 98% or 99%.

Herein, the 90% or more identity can be an identity of at least 90%, 91%, 92%, 93%, 94%, 95%, 96%, 97%, 98% or 99%.

The regulation of the production of L-glutamic acid of a microorganism as described herein can be increasing or reducing the amount of the accumulation of L-glutamic acid in the microorganism (i.e., promoting or inhibiting the biosynthesis of L-glutamic acid).

The present invention also provides a method for increasing the production of L-glutamic acid in a microorganism, the method comprising any one of:

E1) increasing the expression amount, or content of the nucleic acid molecule BBD29_00405$^{G597A}$ in a target microorganism to provide a microorganism having a greater production of L-glutamic acid than the target microorganism;

E2) increasing the expression amount, or content of the DNA molecule of D4) or D5) in a target microorganism to provide a microorganism having a greater production of L-glutamic acid than the target microorganism;

E3) performing a mutation on the DNA molecule whose nucleotide sequence is SEQ ID NO: 1 in the target microorganism to provide a microorganism having a greater production of L-glutamic acid than the target microorganism.

In the method above, the mutation can be a point mutation, i.e., a mutation of a single nucleotide.

In the method above, the point mutation can be a mutation of alanine residue at position 199 in an amino acid sequence coded by the DNA molecule set forth in SEQ ID NO: 1 to another amino acid residue.

In the method above, the point mutation can be a mutation of alanine at position 199 in an amino acid sequence coded by the DNA molecule set forth in SEQ ID NO: 1 to threonine, providing a mutated protein BBD29_00405$^{M199I}$ whose amino acid sequence is SEQ ID NO: 4.

The mutation refers to a change in one or several bases in a gene through site-directed mutation, resulting in a change in the constitution of the amino acids of a corresponding protein, thereby generating a new protein or causing a new function to the original protein, that is, site-directed mutation to genes. Techniques for site-directed mutation to genes such as oligonucleotide primer-mediated site-directed mutation, PCR-mediated site-directed mutation, or cassette mutation are well known to those skilled in the art.

The point mutation as described herein can be replacement of a single base, insertion of a single base, or deletion of a single base, and specifically, replacement of a single base. The replacement of a single base can be allelic replacement.

The point mutation can be performing a nucleic acid modification to guanine (G) at position 597 of the BBD29_00405 gene (SEQ ID NO: 1).

Specifically, the point mutation can be performing a mutation to guanine (G) at position 597 of the BBD29_00405 gene (SEQ ID NO: 1) to adenine (A) to provide a DNA molecule set forth in SEQ ID NO: 2.

Herein, the recombinant vector can be, specifically, recombinant vector pK18-BBD29_00405$^{G597A}$, PK18mobsacB-BBD29_00405, PK18mobsacB-BBD29_00405$^{G597A}$ pXMJ19-BBD29_00405 or pXMJ19-BBD29_00405$^{G597A}$.

The recombinant vector pK18-BBD29_00405$^{G597A}$ contains the DNA molecule set forth as positions 1-1473 of the mutated gene BBD29_00405$^{G597A}$ set forth in SEQ ID NO: 2, and specifically is a recombinant vector obtained by inserting the DNA fragment BBD29_00405$^{G597A}$-Up-Down fragment set forth in SEQ ID NO: 31 between Xba I recognition sites in pK18mobsacB vector, while keeping the other sequences of pK18mobsacB vector unchanged.

The recombinant vector PK18mobsacB-BBD29_00405 is used to integrate an exogenous gene BBD29_00405 into a chromosome of a host, and to overexpress a wild-type BBD29_00405 gene in a producer bacterium.

The recombinant vector PK18mobsacB-BBD29_00405$^{G597A}$ is used to integrate an exogenous gene BBD29_00405$^{G597A}$ to a chromosome of a host, and to overexpress a mutant gene BBD29_00405$^{G597A}$ in a producer bacterium.

The recombinant vector pXMJ19-BBD29_00405 is used to express an exogenous gene BBD29_00405 outside a chromosome via a plasmid, thereby overexpressing a wild-type BBD29_00405 gene in a producer bacterium.

The recombinant vector pXMJ19-BBD29_00405$^{G597A}$ is used to express an exogenous gene BBD29_00405$^{G597A}$ outside a chromosome via a plasmid, thereby overexpressing a mutant gene BBD29_00405$^{G597A}$ in a producer bacterium.

The recombinant vectors pK18-BBD29_00405$^{G597A}$ PK18mobsacB-BBD29_00405, PK18mobsacB-BBD29_00405$^{G597A}$, pXMJ19-BBD29_00405 and pXMJ19-BBD29_00405$^{G597A}$ are all within the scope of protection of the present invention.

Herein, the recombinant microorganism can be, specifically, a recombinant bacterium YPG-025, YPG-026, YPG-027, YPG-028 or YPG-029.

The recombinant bacterium YPG-025 is a recombinant bacterium obtained by transformation of the recombinant vector pK18-BBD29_00405$^{G597A}$ into *Corynebacterium glutamicum* CGMCC No. 21220, and the recombinant bacterium YPG-025 contains the mutated gene BBD29_00405$^{G597A}$ set forth in SEQ ID NO: 2.

The recombinant bacterium YPG-026 contains a double-copy BBD29_00405 gene set forth in SEQ ID NO: 1; a recombinant bacterium containing a double-copy BBD29_00405 gene can significantly and steadily increase the expression amount of BBD29_00405 gene. The recombinant bacterium YPG-026 is an engineered bacterium overexpressing a wild-type BBD29_00405 gene on genome.

The recombinant bacterium YPG-027 contains a mutated BBD29_00405$^{G597A}$ gene set forth in SEQ ID NO: 2; the recombinant bacterium YPG-027 is an engineered bacterium overexpressing a mutant-type BBD29_00405$^{G597A}$ gene on genome.

The recombinant bacterium YPG-028 contains a double-copy BBD29_00405 gene set forth in SEQ ID NO: 1; the recombinant bacterium YPG-028 is an engineered bacterium overexpressing a wild-type BBD29_00405 gene on a plasmid, i.e., overexpression outside a chromosome via a plasmid pXMJ19-BBD29_00405.

The recombinant bacterium YPG-029 contains a mutated BBD29_00405$^{G597A}$ gene set forth in SEQ ID NO: 2; the recombinant bacterium YPG-029 is an engineered bacterium overexpressing a mutant-type BBD29_00405$^{G597A}$ gene on a plasmid, i.e., overexpression outside a chromosome via a plasmid pXMJ19-BBD29_00405$^{G597A}$.

The recombinant bacteria YPG-025, YPG-025, YPG-027, YPG-027 and YPG-029 are all within the scope of protection of the present invention.

The present invention also provides a method for constructing the recombinant microorganism, the method comprising at least one of:

F1) introducing the nucleic acid molecule BBD29_00405$^{G597A}$ into a target microorganism to provide the recombinant microorganism;

F2) introducing the DNA molecule set forth in SEQ ID NO: 1 into a target microorganism to provide the recombinant microorganism;

F3) editing the DNA molecule set forth in SEQ ID NO: 1 with a gene editing measure (such as single-base gene editing) to contain the DNA molecule set forth in SEQ ID NO: 2 in a target microorganism.

The introducing can be host bacterium transformation with a vector bearing a DNA molecule of the present invention through any of known transformation methods, such as a chemical transformation method or an electrotransformation method. The introduced DNA molecule can be single-copy, or multi-copy. The introducing can be integration of an exogenous gene into a chromosome of a host, or expression outside a chromosome via a plasmid.

The present invention also provides a method for preparing L-glutamic acid, the method comprising producing L-glutamic acid with any one of the recombinant microorganisms as described herein.

In the method above, the method can be preparation of L-glutamic acid in a fermentation method, and the recombinant microorganism can be the genus *Corynebacterium*, and specifically, *Corynebacterium glutamicum* and variants thereof.

Reference to Biological Deposit

*Corynebacterium glutamicum* was deposited at China General Microbiological Culture Collection Center, abbreviated as CGMCC, Address: No. 3, Yard 1, Beichen West Road, Chaoyang District, Beijing, Post Code: 100101 on Nov. 23, 2020, with Accession Number of the Biological Deposit: CGMCC No. 21220, Strain Name: YPGLU001.

DETAILED DESCRIPTION

In the following, the technical solutions of the present invention will be further described in detail in connection with specific examples. It should be understood that the following examples merely illustrate and explain the present invention, and should not be construed as limiting the scope of protection of the present invention. All the techniques implemented based on the above contents of the present invention are encompassed in the scope that the present invention intends to protect.

Unless otherwise specified, the raw materials and reagents used in the following examples are all commercially available or can be prepared by known methods. The experimental methods without specific conditions annotated in the following examples usually adhere to routine conditions such as those described in Sambrook et al., Molecular Cloning: Laboratory Manual (New York: Cold Spring Harbor Laboratory Press, 1989), or to those recommended by manufacturers.

Unless otherwise defined or expressly indicated by the background, all the technical and scientific terms in the disclosure have the same meaning as commonly understood by one of ordinary skilled in the art to which the disclosure pertains.

In the following examples, the constitution of the basic medium used to culture the strain is the same, and sucrose, kanamycin or chloramphenicol, etc. are added based on the constitution of the basic medium for a corresponding demand. If a solid one is desired, just add 2% agar, with pH at 7.0 and temperature at 30° C. for culturing. The constitution of solutes in a basic medium is shown in Table 1 below. Dissolve the solutes shown in Table 1 in water to provide a basic medium:

TABLE 1

Constitution of Basic Medium

| Name of Reagent | Compounding Ratio | Fermentation Tank |
|---|---|---|
| Glucose | g/L | 5.0 |
| Phosphoric Acid | g/L | 0.38 |
| Magnesium Sulfate | g/L | 1.85 |
| Potassium Chloride | g/L | 1.6 |
| Biotin | μg/L | 550 |
| Vitamin B1 | μg/L | 300 |
| Ferrous Sulfate | mg/L | 10 |
| Manganese Sulfate | g/dl | 10 |
| $KH_2PO_4$ | g/L | 2.8 |
| Vitamin C | mg/L | 0.75 |
| Vitamin B12 | μg/L | 2.5 |
| Para-Aminobenzoic acid | mg/L | 0.75 |
| Defoamer | ml/dl | 0.0015 |
| Betaine | g/L | 1.5 |
| Cane-Sugar Molasses | ml/L | 7 |
| Corn Steep Liquor | ml/L | 77 |
| Aspartic acid | g/L | 1.7 |
| Hair powder | g/L | 2 |

*Corynebacterium glutamicum* YPGLU001 CGMCC No. 21220 in the following examples has been deposited at China General Microbiological Culture Collection Center (abbreviated as CGMCC, Address: No. 3, Yard 1, Beichen West Road, Chaoyang District, Beijing, Institute of Microbiology, Chinese Academy of Sciences) on Nov. 23, 2020, with Accession No. CGMCC No. 21220. *Corynebacterium glutamicum* YPGLU001 is also known as *Corynebacterium glutamicum* CGMCC No. 21220.

Example 1. Construction of Transformation Vector pK18-BBD29_00405$^{G597A}$ Comprising BBD29_00405 Gene Coding Region with Point Mutation According to the *Corynebacterium glutamicum* ATCC13869 genome (GenBank: CP016335.1) sequence published on NCBI, two pairs of primers are designed and synthesized for amplifying a sequence of a BBD29_00405 gene (GenBank: AKF27993.1) coding zone to introduce a point mutation to the strains ATCC13869 and *Corynebacterium glutamicum YPGLU*001 (Accession Number of the Biological Deposit: CGMCC No. 21220) producing L-glutamic acid in high yield by virtue of allelic replacement. The amino acid sequence corresponding to a coded protein is SEQ ID NO: 3, with a change of guanine (G) at position 597 in the nucleotide sequence of BBD29_00405 gene to adenine (A) (SEQ ID NO: 2: BBD29_00405$^{G597A}$) and thus a change of methionine (M) at position 199 in the amino acid sequence corresponding to the coded protein to isoleucine (I) (SEQ ID NO: 4: BBD29_00405$^{M199I}$).

The nucleotide sequence of a wild-type BBD29_00405 gene is SEQ ID NO: 1 and the amino acid sequence of the BBD29_00405 protein coded by it is SEQ ID NO: 3;

The nucleotide sequence of a mutated BBD29_00405$^{G597A}$ gene is SEQ ID NO: 2 and the amino acid sequence of the mutated BBD29_00405$^{M199I}$ protein coded by it is SEQ ID NO: 4.

The primers are designed as follows (synthesized by Invitrogen Corporation, Shanghai, with mutated base underlined):

```
P1:
                                          (SEQ ID NO: 5)
5'CAGTGCCAAGCTTGCATGCCTGCAGGTCGACTCTAGATGACTATTAAT

GTCTCCGA 3'

P2:
                                          (SEQ ID NO: 6)
5'AGACCGGCATCAAGTATGGTCTGGGCA3'

P3:
                                          (SEQ ID NO: 7)
5'TGCCCAGACCATACTTGATGCCGGTCT3'

P4:
                                          (SEQ ID NO: 8)
5'CAGCTATGACCATGATTACGAATTCGAGCTCGGTACCCCTAGCCGGCG

TAAGGATCCCGGAT 3'
```

Method for Construction: using *Corynebacterium glutamicum* ATCC13869 as a template, PCR amplification is performed with respective primers P1, P2 and P3, P4.

PCR System: 10×Ex Taq Buffer 5 μL, dNTP Mixture (2.5 mM each) 4 μL, Mg 2+(25 mM) 4 μL, primers (10 μM) 2 μL each, Ex Taq (5 U/μL) 0.25 μL, a template 1 μL, with water as balance, in a total volume of 50 μL.

The above PCR amplification is performed by pre-denaturation for 5 min at 94° C., denaturation for 30 s at 94° C., annealing for 30 s at 52° C., and extension for 40 s at 72° C. (30 circles), and overextension for 10 min at 72° C., to provide two DNA fragments containing a BBD29_00405 gene coding region each sized in about 647 bp and 927 bp, respectively, (BBD29_00405$^{G597A}$-Up (SEQ ID NO: 29) and BBD29_00405$^{G597A}$-Down (SEQ ID NO: 30).

After BBD29_00405$^{G597A}$-Up and BBD29_00405$^{G597A}$-Down are isolated via Agarose Gel Electrophoresis and purified, the above two DNA fragments are then used as a template with P1 and P4 as primers for overlap PCR amplification to provide a BBD29_00405$^{G597A}$-Up-Down fragment in 1547 bp in length, having a nucleotide sequence of SEQ ID NO: 31.

PCR System: 10×Ex Taq Buffer 5 μL, dNTP Mixture (2.5 mM each) 4 μL, Mg 2+(25 mM) 4 μL, primers (10 μM) 2 μL each, Ex Taq (5 U/μL) 0.25 μL, a template 1 μL, with water as balance, in a total volume of 50 μL.

The above PCR amplification is performed by pre-denaturation for 5 min at 94° C., denaturation for 30 s at 94° C., annealing for 30 s at 52° C., and extension for 100 s at 72° C. (30 circles), and overextension for 10 min at 72° C.

The DNA fragment causes a change of guanine (G) at position 597 in the BBD29_00405 gene coding zone of the mutagenized strain of ATCC13869, *Corynebacterium glutamicum* YPGLU001 (Accession Number of the Biological Deposit: CGMCC No. 21220), finally resulting in a change of the amino acid at position 199 of a coded protein from methionine (M) to isoleucine (I).

After pK18mobsacB plasmid (purchased from Addgene Corporation) is cleaved with Xba I, the BBD29_00405$^{G597A}$-Up-Down and the linearized pK18mobsacB plasmid are isolated via Agarose Gel Electrophoresis and purified, followed by assembly with NEBuider recombination system (NEB E5520S) to provide vector pK18-BBD29_00405$^{G597A}$ a plasmid containing a kanamycin-resistant marker. And, the vector pK18-BBD29_00405$^{G597A}$ is sent for sequencing and identification in a company for sequencing, while vector pK18-BBD29_00405$^{G597A}$ containing a correct point mutation (G-A) is preserved for reserve.

Recombinant vector pK18-BBD29_00405$^{G597A}$ is a recombinant vector obtained by inserting the DNA fragment BBD29_00405$^{G597A}$-Up-Down fragment set forth in SEQ ID NO: 31 between XbaI recognition sites of pK18mobsacB vector, while keeping the other sequences of pK18mobsacB vector unchanged.

Example 2. Construction of Engineered Strain Comprising BBD29_00405$^{G597A}$ with Point Mutation Method for Construction: plasmid pK18-BBD29_00405$^{G597A}$ following allelic replacement is electrotransformed into *Corynebacterium glutamicum* YPGLU001 producing L-glutamic acid in high yield (Accession Number of the Biological Deposit: CGMCC No. 21220; it is confirmed by sequencing that a wild-type BBD29_00405 gene coding zone is retained on the chromosome of the strain); the cultured mono-colonies are each identified with primer P1 and universal primer M13R for a positive strain with a band in about 1554 bp (SEQ ID NO: 32) following amplification. The positive strain is cultured on a culture medium containing 15% sucrose; and the cultured mono-colonies are cultured on culture media with and without kanamycin, respectively. Strains that grow on a culture medium without kanamycin and do not grow on a culture medium with kanamycin are subjected to further identification by PCR with the primers as follows (synthesized by Invitrogen Corporation, Shanghai).

```
P5:
                                          (SEQ ID NO: 9)
5'AGAAGGCAACCTGCGCATGA 3'

P6:
                                          (SEQ ID NO: 10)
5'ATCGGGTTGGAAATCGCAGA 3';
```

The sequence of the universal primer M13R is follows: M13R: 5'CAG GAA ACA GCT ATG ACC3'.

The above amplified product in 261 bp (SEQ ID NO: 33) from PCR are subjected to denaturation at a high temperature and ice bath before sscp electrophoresis (with an amplified fragment of plasmid pK18-BBD29_00405$^{G597A}$ as a positive control, an amplified fragment of ATCC13869 as a negative control, and water as a blank control). Since fragments are different in their structures, their locations in electrophoresis are different. Thus, a strain having successful allelic replacement is such a strain that the location of its fragment in electrophoresis is inconsistent with that of a negative control fragment and consistent with that of a positive control fragment.

Again, primers P5 and P6 are used for PCR amplification of a target fragment in a strain having successful allelic replacement, which is linked to PMD19-T vector for sequencing. Base sequence alignment is employed to identify a successful or failed replacement; and the mutant strain derived from a successful replacement of *Corynebacterium glutamicum* YPGLU001 producing glutamic acid in high yield (Accession Number of the Biological Deposit: CGMCC No. 21220) is designated as YPG-025.

The recombinant bacterium YPG-025 is a genetically engineered bacterium YPG-025 containing a point mutation (G-A), as obtained by introducing a point mutation G597A to the BBD29_00405 gene coding zone (SEQ ID NO: 1) of *Corynebacterium glutamicum* CGMCC No. 21220 by virtue of allelic replacement, causing a mutation to the position 597 of the gene from G to A, while keeping the other sequences of the gene unchanged.

Compared with *Corynebacterium glutamicum* CGMCC21220, *Corynebacterium glutamicum* YPG-025 differs only in the substitution of the BBD29_00405 gene set forth in SEQ ID NO: 1 in the genome of *Corynebacterium glutamicum* CGMCC21220 with the BBD29_00405$^{G597A}$ gene set forth in SEQ ID NO: 2. SEQ ID NO: 1 and SEQ ID NO: 2 only differ in one nucleotide, at position 597.

Preparation of PAGE and conditions for SSCP electrophoresis are shown in Table 2 below:

TABLE 2

Preparation of PAGE for sscp Electrophoresis

| Ingredients | Concentration at 8% |
|---|---|
| 40% Acrylamide | 8 mL |
| $ddH_2O$ | 26 mL |
| Glycerol | 4 mL |
| 10 * TBE | 2 mL |
| TEMED | 40 µL |
| 10% AP | 600 µL |
| Conditions for Electrophoresis | Electrophoresis Tank Placed into Ice, 1 × TBE Buffer, Voltage 120 V for 10 h |

Example 3. Construction of Engineered Strain with BBD29_00405 or BBD29_00405$^{G597A}$ Gene Overexpressing on Genome According to the *Corynebacterium glutamicum* ATCC13869 genome (GenBank: CP016335.1) sequence published on NCBI, three pairs of primers are designed and synthesized for amplification of upstream and downstream homology arm fragments, and a sequence of a BBD29_00405 gene coding region and a promoter region, so as to introduce BBD29_00405 or BBD29_00405$^{G597A}$ gene into the strain *Corynebacterium glutamicum* YPGLU001 (Accession Number of the Biological Deposit: CGMCC No. 21220) through homologous recombination.

The primers are designed as follows (synthesized by Invitrogen Corporation, Shanghai):

```
P7:
5'CAGTGCCAAGCTTGCATGCCTGCAGGTCGACTCTAGGACCCGCTTGCC

ATACGAAG 3'

P8:
5'CCTACCACGA CGAGCACTAC ATCTACTCAT CTGAAGAATC 3'

P9:
5'GATTCTTCAG ATGAGTAGAT GTAGTGCTCG TCGTGGTAGG 3'

P10:
5'CAAACCAGAG TGCCCACGAA CTAGCCGGCG TAAGGATCCC 3'

P11:
5'GGGATCCTTA CGCCGGCTAG TTCGTGGGCA CTCTGGTTTG 3'

P12:
5'CAGCTATGACCATGATTACGAATTCGAGCTCGGTACCCCATAAGAAAC

AACCACTTCC 3'
```

Method for Construction: using *Corynebacterium glutamicum* ATCC13869 or YPI019 as a template, PCR amplification is performed with primers P7/P8, P9/P10, and P11/P22, respectively, to provide an upstream homologous arm fragment in about 806 bp, a fragment of BBD29_00405 (SEQ ID NO: 34) or BBD29_00405$^{G597A}$ (SEQ ID NO: 36) gene in about 1777 bp, and a downstream homologous arm fragment in about 788 bp (SEQ ID NO: 37). Further, using P7/P12 as primers, amplification is performed with a mixture of the three amplified fragments above as a template to provide an integrated homologous arm fragment upstream-BBD29_00405-downstream (SEQ ID NO: 38) or an integrated homologous arm fragment upstream-BBD29_00405$^{G597A}$-downstream (SEQ ID NO: 39) in 3291 bp. After the PCR reaction is completed, electrophoresis is performed on the amplified products for recovering a desired DNA fragment in about 3291 bp using a Column DNA Gel Recovery Kit, which is ligated, using NEBuider recombination system, to shuttle plasmid PK18mobsacB having been cleaved with Xba I and recovered to provide an integrative plasmid (i.e., a recombinant vector) PK18mobsacB-BBD29_00405 or PK18mobsacB-BBD29_00405$^{G597A}$ The plasmid contains a kanamycin-resistant marker through which a recombinant having a plasmid integrated into genome can be obtained by screening with kanamycin.

pk18mobsacB-BBD29_00405 is a recombinant vector obtained by inserting the integrated homologous arm fragment upstream-BBD29_00405-downstream (SEQ ID NO: 38) between the cleavage sites of Xba I of shuttle plasmid pk18mobsacB.

pk18mobsacB-BBD29_00405 is a recombinant vector obtained by inserting the integrated homologous arm fragment upstream-BBD29_00405$^{G597A}$-downstream (SEQ ID NO: 39) between the cleavage sites of Xba I of shuttle plasmid pk18mobsacB.

PCR System: 10×Ex Taq Buffer 5 µL, dNTP Mixture (2.5 mM each) 4 µL, $Mg^{2+}$ (25 mM) 4 µL, primers (10 µM) 2 µL each, Ex Taq (5 U/µL) 0.25 µL, a template 1 µL, with water as balance, in a total volume of 50 µL.

The above PCR amplification is performed by pre-denaturation for 5 min at 94° C., denaturation for 30 s at 94° C., annealing for 30 s at 52° C., and extension for 180 s at 72° C. (30 circles), and overextension for 10 min at 72° C.

The two integrative plasmids are each electrotransformed into *Corynebacterium glutamicum* YPGLU001 (Accession Number of the Biological Deposit: CGMCC No. 21220), and PCR identification is performed on the cultured mono-colonies with primers P13/P14 for a positive strain containing a fragment in about 1970 bp (SEQ ID NO: 40) from PCR amplification, while a strain without any fragments amplified therefrom is an original one. Having being screened with 15% sucrose, the positive strain is cultured on culture media with and without kanamycin, respectively, and strains that grow on a culture medium without kanamycin and do not grow on a culture medium with kanamycin are further subjected to PCR for identification with primers P15/P16. The bacterium with a fragment amplified therefrom in about 1758 bp (SEQ ID NO: 41) is a strain having BBD29_00405 or BBD29_00405$^{G597A}$ gene integrated into the genome of the strain *Corynebacterium glutamicum* YPGLU001 (Accession Number of the Biological Deposit: CGMCC No. 21220), designated as YPG-026 (without a mutation point) and YPG-027 (with a mutation point).

```
P13:
5' GTCCAAGGTGACGGCCGCAC 3'

P14:
5' AGCTTCGCCGATGTTGCGCA 3'

P15:
5'AGGTTGCACCCGCCATCGCTGCA3'

P16:
5' ATATTCGGCCCAGCAGCAGC 3'
```

The recombinant bacterium YPG-026 is a recombinant bacterium containing a double-copy BBD29_00405 gene set forth in SEQ ID NO: 1, as obtained by integrating the integrated homologous arm fragment upstream-BBD29_00405-downstream (SEQ ID NO: 38) to the genome of the strain *Corynebacterium glutamicum* YPGLU001. The recombinant bacterium containing a double-copy BBD29_00405 gene can significantly and stably increase the expression amount of the BBD29_00405 gene.

The recombinant bacterium YPG027 is a recombinant bacterium containing a mutated BBD29_00405$^{G597A}$ gene set forth in SEQ ID NO: 2, as obtained by integrating the integrated homologous arm fragment upstream-BBD29_00405$^{G597A}$-dowmstream (SEQ ID NO: 39) to the genome of the strain *Corynebacterium glutamicum* YPGLU001.

Example 4. Construction of Engineered Strain Overexpressing BBD29_00405 or BBD29_00405$^{G597A}$ Gene on Plasmid According to the *Corynebacterium glutamicum* ATCC13869 genome (GenBank: CP016335.1) sequence published on NCBI, a pair of primers for amplifying a sequence of a BBD29_00405 gene coding region and a promoter region are designed and synthesized. The primers are designed as follows (synthesized by Invitrogen Corporation, Shanghai).

```
P17:
5' GCTTGCATGCCTGCAGGTCGACTCTAGAGGATCCCCGTAGTGCTCGT

CGTGGTAGG 3'
```

-continued

```
P18:
5' ATCAGGCTGAAAATCTTCTCTCATCCGCCAAAACCTAGCCGGCGTAA

GGATCCCGGAT 3'
```

Method for Construction: using ATCC13869 or YPG-025 as a template, PCR amplification is performed with primers P17/P18 to provide a DNA molecule containing BBD29_00405 (SEQ ID NO: 42) or a DNA molecule containing BBD29_00405$^{G597A}$ (SEQ ID NO: 43) in about 1807 bp. Electrophoresis is performed on the amplified products for recovering a desired DNA fragment in 1807 bp using a Column DNA Gel Recovery Kit, which is ligated, using NEBuider recombination system, to shuttle plasmid pXMJ19 (BioVector NTCC BiovectorpXMJ19) having been cleaved with EcoR I and recovered to provide an overexpression plasmid pXMJ19-BBD29_00405 or pXMJ19-BBD29_00405$^{G597A}$ The plasmid contains a chloramphenicol-resistant marker, and the transformation of the plasmid into the strain can be achieved by screening with chloramphenicol.

PCR System: 10×Ex Taq Buffer 5 μL, dNTP Mixture (2.5 mM each) 4 μL, $Mg^{2+}$ (25 mM) 4 μL, primers (10 μM) 2 μL each, Ex Taq (5 U/μL) 0.25 μL, a template 1 μL, with water as balance, in a total volume of 50 μL.

The above PCR amplification is performed by pre-denaturation for 5 min at 94° C., denaturation for 30 s at 94° C., annealing for 30 s at 52° C., and extension for 100 s at 72° C. (30 circles), and overextension for 10 min at 72° C.

The recombinant vector pXMJ19-BBD29_00405 is a recombinant strain obtained by inserting the DNA molecule containing BBD29_00405 (SEQ ID NO: 42) between the cleavage sites of EcoR I of shuttle plasmid pXMJ19.

The recombinant vector pXMJ19-BBD29_00405$^{G597A}$ is a recombinant strain obtained by inserting the DNA molecule containing BBD29_00405$^{G597A}$ (SEQ ID NO: 43) between the cleavage sites of EcoR I of shuttle plasmid pXMJ19.

Plasmids are each electrotransformed into *Corynebacterium glutamicum* YPGLU001 (Accession Number of the Biological Deposit: CGMCC No. 21220), and PCR identification is performed on the cultured mono-colonies with primers M13R (−48) and P18 for a transformed strain containing a fragment in about 1846 bp (SEQ ID NO: 44) from PCR amplification, designated as YPG-028 (without a mutation point) and YPG-029 (with a mutation point).

The sequence of M13R (−48) is as follows:

```
5'AGCGGATAAC AATTTCACAC AGGA3'
```

The recombinant bacterium YPG-028 contains a double-copy BBD29_00405 gene set forth in SEQ ID NO: 1; the recombinant bacterium YPG-028 is an engineered bacterium overexpressing a wild-type BBD29_00405 gene on a plasmid, i.e., overexpression outside a chromosome via plasmid pXMJ19-BBD29_00405.

The recombinant bacterium YPG-029 contains a mutated BBD29_00405$^{G597A}$ gene set forth in SEQ ID NO: 2; the recombinant bacterium YPG-029 is an engineered bacterium overexpressing a mutant-type BBD29_00405$^{G597A}$ gene on a plasmid, i.e., overexpression outside a chromosome via plasmid pXMJ19-BBD29_00405$^{G597A}$.

Example 5. Construction of Engineered Strain with BBD29_00405 Gene Deleted on Genome According to the *Corynebacterium glutamicum* ATCC13869 genome (GenBank: CP016335.1) sequence published on NCBI, two pairs of primers for amplifying fragments at both ends of a BBD29_00405 gene coding region are synthesized, as upstream and downstream homologous arm fragments. The primers are designed as follows (synthesized by Invitrogen Corporation, Shanghai):

```
P19:
5'CAGTGCCAAGCTTGCATGCCTGCAGGTCGACTCTAGGTCTGGGGGTGA

GCGCGGAT 3'

P20:
AGGAAAATAACGCATCCATCTGCCCCTTTACAAATCCACCGCAAACACTG

GGAT 3'

P21:
TGGATTTGTAAAGGGGCAGATGGATGCGTTATTTTCCTTCACTTTTCGTA

TCCA 3'

P22:
5'CAGCTATGACCATGATTACGAATTCGAGCTCGGTACCCCTCTGGCGCA

TCGAACAGGTCGAAGGA 3'
```

Using *Corynebacterium glutamicum* ATCC13869 as a template, PCR amplification is performed with primers P19/P20 and P21/P22, respectively, to provide an upstream homologous arm fragment in 709 bp (SEQ ID NO: 45) and a downstream homologous arm fragment in 734 bp (SEQ ID NO: 46). Further, primers P19/P22 are used for an OVER PCR to provide an integral homologous arm fragment in 1405 bp (SEQ ID NO: 47). After the PCR reaction is completed, electrophoresis is performed on the amplified products for recovering a desired DNA fragment in 1405 bp using a Column DNA Gel Recovery Kit, which is ligated, by virtue of NEBuider recombination system, to a shuttle plasmid, plasmid pk18mobsacB, having been cleaved with Xba I and recovered to provide a knockout plasmid. The plasmid contains a kanamycin-resistant marker.

The knockout plasmid is electrotransformed into *Corynebacterium glutamicum* YPGLU001 (Accession Number of the Biological Deposit: CGMCC No. 21220), and PCR identification is performed on the cultured mono-colonies each with the following primers (synthesized by Invitrogen Corporation, Shanghai):

```
P23:
5'GTCTGGGGGTGAGCGCGGAT3'

P24:
5'CTCTGGCGCATCGAACAGGTCGAAGGA 3'
```

A strain with bands in about 1331 bp (SEQ ID NO: 49) and about 2804 bp (SEQ ID NO: 48) amplified from the above PCR amplification is a positive one, while a strain with just a band in 2804 bp amplified therefrom is a starting one. Having being screened on a culture medium with 15% sucrose, the positive strain is cultured on culture media with and without kanamycin, respectively, and strains that grow on a culture medium without kanamycin and do not grow on a culture medium with kanamycin are subjected further to PCR identification with primers P23/P24. The strain with a band in 1331 bp amplified therefrom is a genetically engineered strain with the BBD29_00405 gene coding region knocked out, designated as YPG-030.

The recombinant bacterium YPG-030 is one having the BBD29_00405 gene on the genome of *Corynebacterium glutamicum* CGMCC No. 21220 knocked out.

Example 6. Experiments on Fermentation of L-Glutamic Acid

Experiments on fermentation are performed on the strains YPG-025, YPG-026, YPG-027, YPG-028, YPG-029 and YPG-030 as constructed in Examples 2-5, and an original *Corynebacterium glutamicum* YPGLU001 (Accession Number of the Biological Deposit: CGMCC No. 21220) in a fermentation tank, BLBIO-5GC-4-H type (purchased from Shanghai Bailun Biological Technology Co., Ltd.) with the culturing medium shown in Table 3 and the control process for fermentation shown in Table 4, and products from fermentation are collected.

At the initial moment when seeding is completed, the bacterium is at a concentration of 15 g/L in the system. During the fermentation: sugar content in the system (residual sugar) is controlled by supplementing an aqueous solution containing 50-55% glucose.

Triplicates are made for each strain. Results are shown in Table 5.

TABLE 3

Formulation of Solutes in Culture Medium for Fermentation

| Name of Reagent | Compounding Ratio |
|---|---|
| Glucose | 5.0 g/L |
| Phosphoric Acid | 0.38 g/L |
| Magnesium Sulfate | 1.85 g/L |
| Potassium Chloride | 1.6 g/L |
| Biotin | 550 μg/L |
| Vitamin B1 | 300 μg/L |
| Ferrous Sulfate | 10 mg/L |
| Manganese Sulfate | 10 g/dL |
| $KH_2PO_4$ | 2.8 g/L |
| Vitamin C | 0.75 mg/L |
| Vitamin B12 | 2.5 μg/L |
| Para-Aminobenzoic acid | 0.75 mg/L |
| Defoamer | 0.0015 mL/dL |
| Betaine | 1.5 g/L |
| Cane-Sugar Molasses | 7 mL/L |
| Corn Steep Liquor | 77 mL/L |
| Aspartic acid | 1.7 g/L |
| Hair powder | 2 g/L |

The above culturing medium for fermentation is one obtained by dissolving the solutes shown in Table 3 in water.

TABLE 4

Control Process for Fermentation

| | Condition | | | |
|---|---|---|---|---|
| Cycle | Revolutions Per Minute | Air Volume | Pressure | Temperature for Culturing |
| 0 h | 400 rpm | 3 L/min | 0.05 MPA | 32.5° C. |
| OD 1.0 | 600 rpm | 5 L/min | 0.08 MPA | 37° C. |
| OD 1.4 | 700 rpm | 7 L/min | 0.11 MPA | 38° C. |
| 34 h-36 h | End of Fermentation, 50-20% Dissolved Oxygen as Standard for Increasing and Decreasing Air Volume during Control Process | | | |
| pH | Controlled at 7.0 at 0 h; Controlled at 6.8 at 14 h | | | |
| Control of Fed-Batch Sugar | Fed-Batch Sugar at Concentration of 50-55% in Fermentation Tank Residual Sugar Controlled at 0.5-1.0% in Fermentation Tank | | | |

TABLE 5

Results of Experiments on Fermentation of L-glutamic Acid

| Strain | Production of L-Glutamic Acid (g/L) | OD (562 nm) |
|---|---|---|
| *Corynebacterium glutamicum* YPGLU001 | 97.6 | 41.5 |
| YPG-025 | 96.1 | 40.3 |
| YPG-026 | 98.3 | 42.9 |
| YPG-027 | 101.5 | 41.6 |
| YPG-028 | 99.7 | 41.1 |
| YPG-029 | 102.9 | 40.8 |
| YPG-030 | 89.4 | 41.4 |

Results from Table 5 show that, in an engineered bacterium producing L-glutamic acid, *Corynebacterium glutamicum* YPGLU001 (Accession Number of the Biological Deposit: CGMCC No. 21220), point mutation to the BBD29_00405 gene coding region, BBD29_00405$^{G597A}$ facilitates an increase in the production of L-glutamic acid; overexpression of BBD29_00405 or BBD29_00405$^{G597A}$ facilitates to increase the production of L-glutamic acid, while knocking out the BBD29_00405 gene is adverse to the accumulation of L-glutamic acid.

The embodiments of the present invention have been illustrated above. However, the present invention is not limited to the above embodiments. Any modification, equivalent substitution, improvement, etc. made within the spirit and principle of the invention should be included in the scope of protection of the present invention.

INDUSTRIAL APPLICATION

The present invention has found out that, by knocking out the BBD29_00405 gene, the product coded by the gene has an effect on L-glutamic acid production capacity, and that a recombinant strain obtained by introducing a point mutation to the coding sequence, or by increasing the copy number of, or overexpressing the gene facilitates production of L-glutamic acid at a higher concentration as compared with an unmodified strain. When the inhibitor of CTD-2256P15.2 or the micropeptide PACMP coded by it provided by the present invention acts on tumor cells or tumor tissues, the growth of tumor cells can be remarkably inhibited, the apoptosis of tumor cells can be increased, the tumor volume can be reduced, and an excellent anti-tumor effect can be achieved. The novel anti-tumor drugs combination scheme provided by the present invention, use of the inhibitor of CTD-2256P15.2 or the micropeptide PACMP coded by it in combination with other anti-tumor drugs, can significantly enhance the killing effect of the anti-tumor drugs on tumor cells and reduce the resistance of tumor cells to chemotherapy, thereby improving the clinical treatment effect on tumors. CTD-2256P15.2 is highly expressed in chemotherapy-resistant tumor tissues and cell lines, and its high expression is significantly negatively correlated with progression-free survival and overall survival of patients with tumors. The CTD2256P15.2 gene expression level provided by the present invention can be used as a molecular index for predicting the sensitivity to chemotherapy and prognosis of patients with tumors, creating a new standard for an effective guide to clinical chemotherapeutic medication for patients with tumors and evaluating the prognosis of treatment.

Specifically, the present invention first constructs a genetically engineered bacterium YPG-025 with a point mutation (G-A) by introducing a point mutation to a BBD29_00405 gene coding region (SEQ ID NO: 1) of *Corynebacterium glutamicum* CGMCC No. 21220 via allelic replacement. In order to further investigate and verify that overexpressing a wild-type BBD29_00405 gene or a mutant gene BBD29_00405$^{G597A}$ thereof in a producer bacterium can increase the production of L-glutamic acid, an exogenous gene is integrated into the chromosome of a host, or expressed outside the chromosome by a plasmid, respectively, thereby constructing engineered bacteria YPG-026, YPG-027, YPG-028 and YPG-029 overexpressing BBD29_00405 gene or BBD29_00405$^{G597A}$ gene on genome and plasmid. Experiments suggest that BBD29_00405 gene and variants thereof are involved in the biosynthesis of L-glutamic acid. By overexpressing or knocking out BBD29_00405 gene, or having site-directed mutation (such as point mutation) thereto, the amount of accumulation of L-glutamic acid in a microorganism can be regulated. Point mutation to the BBD29_00405 gene coding region or overexpression of BBD29_00405 gene or a mutant gene BBD29_00405$^{G597A}$ thereof in a producer bacterium facilitates an increase in the production and conversion rate of L-glutamic acid, while knocking out or weakening the BBD29_00405 gene is adverse to the accumulation of L-glutamic acid. BBD29_00405 gene and a variant thereof (such as BBD29_00405$^{G597A}$ gene) can be used to construct a genetically engineered strain for producing L-glutamic acid to promote an increase in the production of L-glutamic acid, and to breed a high-production and high-quality strain for industrialized production, which finds values in a wide range of applications to, and is of important economic significance for industrialized production of L-glutamic acid.

What is claimed is:

1. An isolated protein, wherein the protein is any one of:

A1) a protein comprising the amino acid sequence of SEQ ID NO: 4; or

A2) a protein consisting of the amino acid sequence of SEQ ID NO: 3, wherein methionine at position 199 is substituted with isoleucine.

* * * * *